(12) United States Patent
Chetlapalli et al.

(10) Patent No.: US 10,143,581 B2
(45) Date of Patent: Dec. 4, 2018

(54) DYNAMIC TENSION SYSTEM FOR ORTHOPEDIC DEVICE

(71) Applicant: OSSUR HF, Reykjavik (IS)

(72) Inventors: Janaki Ram-srinivasaRao Chetlapalli, Irvine, CA (US); Harry Duane Romo, Aliso Viejo, CA (US); Jane Lee, Fullerton, CA (US); Gudni Ingimarsson, Reykjavik (IS); Derek Brookover, Irvine, CA (US); Michael Meritt-Powell, Oceanside, CA (US); Jared Olivo, Highland, CA (US)

(73) Assignee: OSSUR HF, Reykjavik (IS)

( * ) Notice: Subject to any disclaimer, the term of this patent is extended or adjusted under 35 U.S.C. 154(b) by 916 days.

(21) Appl. No.: 14/311,548

(22) Filed: Jun. 23, 2014

(65) Prior Publication Data

US 2015/0005685 A1    Jan. 1, 2015

Related U.S. Application Data

(60) Provisional application No. 61/893,323, filed on Oct. 21, 2013, provisional application No. 61/838,217, filed on Jun. 21, 2013.

(51) Int. Cl.
*A61F 5/01*    (2006.01)

(52) U.S. Cl.
CPC .......... *A61F 5/0125* (2013.01); *A61F 5/0123* (2013.01); *A61F 2005/0132* (2013.01)

(58) Field of Classification Search
CPC ...... A61F 5/05; A61F 5/05841; A61F 5/0585; A61F 5/05858; A61F 5/05866;
(Continued)

(56) References Cited

U.S. PATENT DOCUMENTS

| 73,768 A | 1/1868 | Allen |
|---|---|---|
| 1,601,659 A | 9/1926 | Van Harlingen |

(Continued)

FOREIGN PATENT DOCUMENTS

| DE | 33 20 274 A1 | 12/1984 |
|---|---|---|
| DE | 196 31 632 A1 | 2/1998 |

(Continued)

OTHER PUBLICATIONS

DeFrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

(Continued)

*Primary Examiner* — Kari Rodriquez
*Assistant Examiner* — Camtu Nguyen
(74) *Attorney, Agent, or Firm* — Workman Nydegger

(57) ABSTRACT

A dynamic tension system connects to an orthopedic device having a frame and a hinge connected to the frame. The dynamic tension system includes a cable, an adjustment mechanism connected to the cable and arranged to incrementally wind or release the cable, and a tension control device connected to the adjustment mechanism and arranged to limit the adjustment mechanism from winding of the cable past a predetermined tension level.

12 Claims, 11 Drawing Sheets

(58) Field of Classification Search
CPC .................. A61F 5/0123; A61F 5/0125; A61F 2005/0132; B25B 23/14; B25B 23/1405; B25B 14/142; B25B 25/1415; B25B 25/1422; B25B 25/1427
USPC ..................... 602/16, 20, 23, 26; 128/882; 242/388.1–388.3, 396, 396.1, 396.2, 242/396.4
See application file for complete search history.

(56) References Cited

U.S. PATENT DOCUMENTS

| | | |
|---|---|---|
| 2,195,024 A | 3/1940 | Bullock |
| 2,467,907 A | 4/1949 | Peckham |
| 2,536,454 A | 1/1951 | McIntyre |
| 2,558,986 A | 7/1951 | Seelert |
| 2,959,168 A | 11/1960 | Shook |
| 3,316,900 A | 5/1967 | Young |
| 3,348,812 A * | 10/1967 | Story .................. F16G 11/12 254/223 |
| 3,444,560 A | 5/1969 | Northup, Jr. |
| 3,753,625 A | 8/1973 | Fabrizio et al. |
| 3,947,156 A | 3/1976 | Becker |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,397,308 A | 8/1983 | Hepburn |
| 4,407,276 A | 10/1983 | Bledsoe |
| 4,428,369 A | 1/1984 | Peckham et al. |
| 4,433,679 A | 2/1984 | Mauldin et al. |
| 4,463,751 A | 8/1984 | Bledsoe |
| 4,489,718 A | 12/1984 | Martin |
| 4,506,661 A | 3/1985 | Foster |
| 4,508,111 A | 4/1985 | Hepburn |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,657,000 A | 4/1987 | Hepburn |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spadman |
| 4,856,501 A | 8/1989 | Castillo et al. |
| 4,865,024 A | 9/1989 | Hensley et al. |
| 4,884,760 A * | 12/1989 | Baggio .................. A43C 11/16 24/68 SK |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A | 3/1991 | Spademan |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,357,654 A | 10/1994 | Hsing-Chi |
| 5,437,611 A | 8/1995 | Stern |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,575,764 A | 11/1996 | Van Dyne |
| 5,588,956 A | 12/1996 | Billotti |
| 5,599,288 A | 2/1997 | Shirley et al. |
| 5,624,390 A | 4/1997 | Van Dyne |
| 5,628,722 A | 5/1997 | Solomonow et al. |
| 5,658,241 A | 8/1997 | Deharde et al. |
| 5,662,596 A | 9/1997 | Young |
| 5,683,353 A | 11/1997 | Hamersly |
| 5,685,830 A | 11/1997 | Bonutti |
| 5,807,294 A | 9/1998 | Cawley et al. |
| 5,827,208 A | 10/1998 | Mason et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Sterns et al. |
| 5,921,946 A | 7/1999 | Tillinghast et al. |
| 5,934,599 A * | 8/1999 | Hammerslag ............ A43C 1/00 242/396.1 |
| 5,950,245 A | 9/1999 | Binduga |
| 5,954,677 A | 9/1999 | Albrecht et al. |
| 5,997,493 A | 12/1999 | Young |
| 6,001,075 A | 12/1999 | Clemens et al. |
| 6,004,283 A | 12/1999 | Young |
| 6,074,355 A | 6/2000 | Bartlett |
| 6,110,137 A | 8/2000 | Bastyr et al. |
| 6,110,138 A | 8/2000 | Shirley |
| 6,129,690 A | 10/2000 | Hamlin et al. |
| RE37,209 E | 6/2001 | Hensley et al. |
| 6,245,034 B1 | 6/2001 | Bennett et al. |
| RE37,297 E | 7/2001 | Smith, III |
| 6,290,664 B1 | 9/2001 | Nauert |
| 6,331,169 B1 | 12/2001 | Bastyr et al. |
| 6,409,693 B1 | 6/2002 | Brannigan |
| 6,413,232 B1 | 7/2002 | Townsend et al. |
| 6,425,166 B1 | 7/2002 | Seligman et al. |
| 6,436,058 B1 | 8/2002 | Krahner et al. |
| 6,471,664 B1 | 10/2002 | Campbell et al. |
| 6,500,138 B1 | 12/2002 | Irby et al. |
| 6,551,264 B1 | 4/2003 | Cawley et al. |
| 6,666,837 B2 | 12/2003 | Weihermuller |
| 6,740,054 B2 | 5/2004 | Sterns |
| 6,752,775 B2 | 6/2004 | Seligman et al. |
| 6,834,752 B2 | 12/2004 | Irby et al. |
| 6,875,187 B2 | 4/2005 | Castillo |
| 6,936,020 B2 | 8/2005 | Davis |
| 6,993,808 B1 | 2/2006 | Bennett et al. |
| 7,004,919 B2 | 2/2006 | Gaylord et al. |
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,960 B2 | 4/2007 | Kenney |
| 7,235,058 B2 | 6/2007 | Doty et al. |
| 7,235,059 B2 | 6/2007 | Mason et al. |
| 7,309,322 B2 | 12/2007 | Albrecht et al. |
| 7,311,687 B2 | 12/2007 | Hoffmeier et al. |
| D577,828 S | 9/2008 | Ingimundarson et al. |
| 7,431,708 B2 | 10/2008 | Sreeramagiri |
| 7,435,234 B2 | 10/2008 | Gamada |

(56) References Cited

U.S. PATENT DOCUMENTS

| | | |
|---|---|---|
| 7,485,103 B2 | 2/2009 | Mason et al. |
| 7,500,957 B2 | 3/2009 | Bledsoe |
| 7,534,217 B2 | 5/2009 | Seligman et al. |
| 7,534,219 B2 | 5/2009 | Sterns |
| 7,544,174 B2 | 6/2009 | Nathanson |
| 7,553,289 B2 | 6/2009 | Cadichon |
| 7,597,675 B2 | 10/2009 | Ingimundarson et al. |
| 7,662,122 B2 | 2/2010 | Sterling |
| 7,722,555 B2 | 5/2010 | Doty et al. |
| 7,727,174 B2 | 6/2010 | Chang et al. |
| 7,749,183 B2 | 7/2010 | Ingimundarson et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,927,299 B2 | 4/2011 | Krause |
| 7,963,933 B2 | 6/2011 | Nace |
| 8,048,013 B2 | 11/2011 | Ingimundarson et al. |
| 8,128,587 B2 | 3/2012 | Stevenson et al. |
| 8,376,974 B2 | 2/2013 | Nace |
| 8,882,688 B1 | 11/2014 | Ancinec |
| 8,920,350 B2 | 12/2014 | Merkley et al. |
| 9,220,624 B2 | 12/2015 | Jansson et al. |
| 9,351,864 B2 | 5/2016 | Romo et al. |
| 9,539,135 B2 | 1/2017 | Romo et al. |
| 2002/0013544 A1 | 1/2002 | Stearns |
| 2002/0052568 A1 | 5/2002 | Houser et al. |
| 2002/0052663 A1 | 5/2002 | Herr et al. |
| 2002/0133108 A1 | 9/2002 | Jagodzinski |
| 2004/0002674 A1 | 1/2004 | Sterling |
| 2004/0030411 A1 | 2/2004 | Gaspers |
| 2004/0049140 A1 | 3/2004 | Doty et al. |
| 2004/0049290 A1 | 3/2004 | Bedard |
| 2004/0054307 A1 | 3/2004 | Mason et al. |
| 2004/0054311 A1 | 3/2004 | Sterling |
| 2004/0068215 A1 | 4/2004 | Adelson et al. |
| 2004/0097859 A1 | 5/2004 | Sterns |
| 2005/0015156 A1 | 1/2005 | Hikichi |
| 2005/0020951 A1 | 1/2005 | Gaylord et al. |
| 2005/0177082 A1 | 8/2005 | Bledsoe |
| 2005/0245853 A1 | 11/2005 | Scorvo |
| 2005/0273025 A1 | 12/2005 | Houser |
| 2006/0100560 A1 | 5/2006 | Gilmour |
| 2006/0100561 A1 | 5/2006 | Gilmour |
| 2006/0116616 A1 | 6/2006 | Albrecht et al. |
| 2006/0135902 A1 | 6/2006 | Ingimundarson et al. |
| 2006/0142680 A1 | 6/2006 | Iarocci |
| 2007/0010772 A1 | 1/2007 | Ryan |
| 2007/0050044 A1 | 3/2007 | Haynes et al. |
| 2007/0100265 A1 | 5/2007 | Gamada |
| 2007/0232972 A1 | 10/2007 | Martinez |
| 2007/0270976 A1 | 11/2007 | DeHarde et al. |
| 2008/0051684 A1 | 2/2008 | Gamada |
| 2008/0066272 A1 | 3/2008 | Hammerslag et al. |
| 2008/0195013 A1 | 8/2008 | Ingimundarson et al. |
| 2008/0200856 A1 | 8/2008 | Cadichon |
| 2008/0249448 A1 | 10/2008 | Stevenson et al. |
| 2008/0294079 A1 | 11/2008 | Sterling et al. |
| 2009/0054819 A1 | 2/2009 | Einarsson |
| 2009/0076426 A1 | 3/2009 | Einarsson et al. |
| 2009/0099495 A1 | 4/2009 | Campos et al. |
| 2009/0099562 A1 | 4/2009 | Ingimudarson et al. |
| 2009/0105622 A1 | 4/2009 | Sterling et al. |
| 2009/0124948 A1 | 5/2009 | Ingimundarson et al. |
| 2009/0171469 A1 | 7/2009 | Thorsteinsson et al. |
| 2009/0240181 A1 | 9/2009 | Sreeramagiri et al. |
| 2009/0259154 A1 | 10/2009 | Nace |
| 2009/0281637 A1 | 11/2009 | Martin |
| 2009/0287128 A1 | 11/2009 | Ingimundarson et al. |
| 2010/0010409 A1 | 1/2010 | Bejarano |
| 2010/0056970 A1 | 3/2010 | Nace |
| 2010/0162539 A1 | 7/2010 | Rancon |
| 2011/0098618 A1 | 4/2011 | Fleming |
| 2011/0270413 A1 | 11/2011 | Haynes |
| 2012/0022667 A1 | 1/2012 | Accinni et al. |
| 2012/0046585 A1 | 2/2012 | Lee et al. |
| 2012/0059296 A1 | 3/2012 | Kompa |
| 2012/0157902 A1 | 6/2012 | Castillo et al. |
| 2013/0110020 A1* | 5/2013 | Ingimundarson ..... A61F 5/0123 602/16 |
| 2013/0150761 A1 | 6/2013 | Romo et al. |
| 2013/0172797 A1 | 7/2013 | Merkley et al. |
| 2013/0178771 A1 | 7/2013 | Moir et al. |
| 2013/0331754 A1 | 12/2013 | Dunn et al. |
| 2016/0120683 A1 | 5/2016 | Romo et al. |
| 2016/0151189 A1 | 6/2016 | Romo et al. |

FOREIGN PATENT DOCUMENTS

| | | |
|---|---|---|
| DE | 196 45 076 A1 | 5/1998 |
| DE | 198 11 925 A1 | 10/1999 |
| DE | 102 59 751 A1 | 7/2004 |
| DE | 10 2010 006 089 A1 | 8/2010 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| WO | WO 85/01204 * | 3/1985 |
| WO | 86/04228 A1 | 7/1986 |
| WO | WO 95/22700 * | 8/1995 |
| WO | 95/27451 A1 | 10/1995 |
| WO | 96/16615 A1 | 6/1996 |
| WO | 2004/056293 A1 | 7/2004 |
| WO | 2006/044423 A2 | 4/2006 |
| WO | 2009126724 A2 | 10/2009 |
| WO | 2010/087899 A2 | 8/2010 |

OTHER PUBLICATIONS

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom 7 OTS Knee Brace, "Application Instructions & Patient Manual", Jan. 2007, pp. 1-4, vol. CP020223, Rev B, Publisher: Bledsoe Brace Systems, Published in: US. http://www.bledsoebrace.com/pdf/Al/Axiom-Al.pdf.

Brochure: Armor Fourcepoint, Donjoy Product pages http://www.donjoy.com/armorfp. Downloaded, Oct. 2011, p. 2. Published: US.

Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", Bregg 360 Customer Care, Product page http://www.breg.com/knee-bracing/oa/fusion-xt-oa.html, downloaded, Oct. 2011, 2 pages. Publisher: Orthofix, Published in: US.

Brochure: "CTI Custom", Ossur Product page from http://www.ossur.com/?PageID=13230 downloaded, Oct. 2011, 2 pages. Publisher: Ossur Americas, Published in: US.

(56) References Cited

OTHER PUBLICATIONS

Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.

International Search Report and Written Opinion of the International Searching Authority from International Application No. PCT/US2011/051627, dated Jan. 6, 2012.

International Search Report from International Application No. PCT/US2012/062702, dated Feb. 15, 2013.

International Preliminary Report on Patentability from International Application No. PCT/US2011/051627, dated Mar. 28, 2013.

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf.

Extended European Search Report from EP Application No. 12150517.6, dated May 22, 2012.

Smith, Sean D. et al., "Functional bracing of ACL injuries: current state and future directions", Knee Surgery Sports Traumatology Arthhroscopy, Springer, Apr. 27, 2013, 11 pages.

International Search Report and Written Opinion of the International Searching Authority from International Application No. PCT/US2014/013245, dated May 6, 2014.

Jansson, Kyle S. et al., "A Historical Perspective of PCL Bracing", Knee Surgery Sports Traumatology Arthhroscopy, Springer-Verlag, May 24, 2012, 7 pages.

International Search Report from corresponding International Application No. PCT/US2014/042989, dated Oct. 15, 2014.

\* cited by examiner

DYNAMIC TENSION SYSTEM FOR ORTHOPEDIC DEVICE

TECHNICAL FIELD

The present disclosure relates to an improved dynamic tension system for tensioning and preventing overtensioning forces or in a mechanism to create compressive load on a wearer's anatomy, and associated features for use therewith.

BACKGROUND

Conventional orthopedic braces embody a wide range of structures and serve the similar purpose of supporting and stabilizing a joint when worn on the body of a user. When used in this manner, such braces may help an existing injury heal, or prevent future injuries from occurring. A brace can add support and stability to a healthy skeletal joint to reduce the risk of injury when the joint is subjected to undue stress. Alternatively, braces may help provide relief and restore functionality to an injured person by providing stabilizing support to a weakened skeletal joint to reinforce it and reduce the risk of sustaining further injury. An orthopedic brace must be sufficiently secured to a user so it can provide the necessary support and stability as needed.

Patients commonly wear orthopedic knee braces after surgery for treatment of an injury to the knee joint. Knee braces may serve many purposes. For instance, they stabilize the knee joint and control its lateral movement, or knee braces help limit joint flexion and/or extension in an adjustable and controllable manner to prevent recurrence of injury to the knee.

Certain types of knee injuries require special attention. An injury of the posterior cruciate ligament (PCL) would benefit from a PCL knee brace designed to provide support to the back of the upper calf throughout the range of motion to prevent unwanted shifting. In a recently injured or post-operative patient, this may also lessen the lengthening of the PCL during healing. For a patient with a PCL having healed in a lengthened state, the brace may prevent such undesirable shifting to give the patient the feeling of added stability. The tension in the PCL changes dynamically relative to the knee flexion angle. Therefore, the PCL brace may theoretically apply a correspondingly dynamic load to offset the tension in the posterior cruciate ligament.

Conventional PCL braces offer a strap that provides static ACL (anterior cruciate ligament) or PCL support, and such strap is often incorporated into a brace providing multiple ligaments stabilization. No known solutions have been provided which offer a dynamic load specifically on the PCL, and an objective of the disclosure is to provide a dynamic tensioning system for an orthopedic device.

One type of an ACL brace is found in U.S. Pat. No. 7,811,242 and features a hinge arranged to dampen a knee as it goes into extension. A posterior force is applied to the tibia, preventing anterior movement, which stresses the ACL, and reducing the anterior translation. The hinge is arranged to increase knee flexion angles to dampen knee extension and reduce shear forces at the knee.

Another example found in U.S. Pat. Nos. 5,954,677 and 7,309,322 describes a PCL brace arranged to specifically rehabilitate a knee by providing an anteriorly directed tibial force by spring tension to a patient's leg and weight. The load exerted on the knee is constant or static over the entire range of motion.

There are various ways to secure and tighten an orthopedic brace to the body of a user. Many knee braces use straps that attach to a brace frame via clips or tabs, such as D-rings. These straps often secure the brace to a user's leg above and below the knee. Adjustable straps, such as those employing a hook and loop technique utilizing Velcro®, must be manually tightened so that when tension applies to each strap, the brace is urged closer against the user's body. Shortening or lengthening the straps causes the fit of the brace to be tightened or loosened, respectively.

Manually adjusting straps on a brace in this manner is cumbersome and can be quite time consuming, especially when there are multiple straps on a single brace and the user must constantly readjust the tension in each strap. Manually adjusting each strap is an inaccurate way to gauge the general fit of the brace on a user. It is difficult to determine how much a knee brace should be tightened by separate straps that secure the top and bottom portions of the brace to a user's leg above and below the knee, respectively. This is because each strap must be tightened individually and may require a different amount of tension.

Another way of securing an orthopedic brace to the body of a user is by threading a lace in a zigzag pattern through slots on opposite parallel sides of the brace. Pulling each end of the lace creates tension that urges the threaded brace against a user. This lacing system has many drawbacks. For instance, it is difficult to ensure an even distribution of tension along the entire length of the lace due to the slack created around each slot. Higher tensioned portions of the lace, such as those near the ends, cause the brace to be tighter in certain areas. This uneven tensioning can adversely affect the function of the brace, and make it uncomfortable to wear. It is difficult to untighten or redistribute tension in these lacing systems since the user must loosen both ends of the lace, which are often knotted to maintain the initial tension.

Conventional dial tensioning systems also exist for regulating the tension applied to an attached cable. Such systems often incorporate an internal helically wound band spring interposed between the dial and an inner housing. There are also drawbacks to these types of tensioning systems, including the ease by which they can be overtightened. This makes gauging how much a cable or wire has already been tensioned very inaccurate. Traditionally, a user adjusts the cable until he or she feels that it is sufficiently tight. This requires a fair bit of guesswork on behalf of the user.

One of the objectives of the present disclosure is to provide a tightening system with a dynamic tension system that automatically distributes equal lateral tightening forces to a cable, and also makes it easy to determine tension in the cable while it is being tightened.

Adjusting the tension used to secure a brace to a user affects its function, fit and comfort. The ability to increase the tension applied is important because insufficient tension can prevent the brace from staying in place on the limb, and diminish its ability to stabilize or protect the limb. Overtightening the brace by applying too much tension, however, can restrict the individual's blood flow and make the brace very uncomfortable to wear. Therefore, it is another object of the present disclosure to provide a tightening system with an adjustment mechanism that prevents or reduces such overtightening.

It may be desirable to apply loads to various portions of a wearer's anatomy according to desired treatment of the wearer's anatomy. Because of injury risk, there is exists a need to carefully regulate the degree of the load to prevent the wearer from applying an excessive load.

Many orthopedic braces have tightening means that make the brace bulky, difficult to don and properly tighten, difficult to configure, and uncomfortable to wear. There exists a substantial need for a tightening system with an adjustment mechanism that can be quickly and easily adjusted during use, including during either extension or flexion of the brace. It is preferable that a user can adjust the adjustment mechanism by using just one hand, and that the user knows when an initial desired loading has been achieved. Finally, it is desirable that the tightening system can be easily loosened and incrementally adjusted without losing tension in the cable due to continued use. There also exists a need in certain applications of applying a load against the anatomy and regulating the degree of the load. The present disclosure addresses all of these aforementioned needs and other needs addressed or flowing from the below discussion.

SUMMARY

Under the embodiments described, a dynamic tension system includes an adjustment mechanism for preventing a tensioning element such as a cable from being overtightened. Various orthopedic devices, such as a knee brace, may employ a dynamic tension system, which controls tension in the brace. The adjustment mechanism is configured to prevent overtensioning at initial tensioning and/or during use. The user can adjust the fit of the brace to the limb and correspondingly adjust the support that the brace provides.

An embodiment of the dynamic tension system is arranged for an orthopedic device having a frame and at least one hinge connected to the frame. The dynamic tension system comprises a cable, an adjustment mechanism connected to the cable and arranged to incrementally wind or release the cable, and a tension control device connected to the adjustment mechanism and arranged to limit the adjustment mechanism from winding the cable past a predetermined tension level that may be short of or fully winding the cable to a preferable cable tension suitable for desired treatment.

The adjustment system includes a spool arranged to wind the cable and defines a plurality of teeth about a periphery thereof. A pawl is pivotable relative to and is arranged to engage the plurality of teeth. A base retains the spool and the spool is arranged to rotate relative to the base. The pawl is pivotally mounted to the base. A spring engages the pawl and biases the pawl toward the plurality of teeth. A first end of the spring biases against the base and an opposed second end of the spring biases against the pawl.

An access is arranged for disengaging the pawl from the spool, and may define an opening formed by the base. The pawl may define an access feature enabling movement of the pawl from the spool via the access. The base may define a cavity arranged for retaining the spool and has a profile accommodating a shape of the spool.

The base may define a boss about which the spool rotates and may include a pin at which a first end of the pawl pivots so an opposed second end of the pawl can engage or disengage from the plurality of teeth. The base may define an enclosure arranged to receive and retain the first end of the spring. The base may define at least one channel arranged to direct movement of the cable relative to the base and from the spool.

The dynamic tension system may have a shroud arranged to cover the adjustment mechanism, and defines an opening arranged for providing access to the adjustment mechanism. A plate, inclusive of covers, stickers, or other suitable means for covering or blocking, may be arranged to selectively secure over the opening to prevent access to the adjustment mechanism.

The tension control device may be a torque-limiting tool arranged to fail upon reaching a predetermined level of tension in the cable, in that tension in winding at the predetermined level of tension causes the torque-limiting tool to fail. The tension control device is adapted to extend through the opening to engage the adjustment mechanism and selectively rotate the spool. The torque-limiting tool may have a key arranged to be received, and engage a keyhole defined by the adjustment mechanism for winding of the cable. A seal element, inclusive of covers, stickers, or other suitable means for covering or blocking, may be provided to secure over the keyhole to prevent tampering of the adjustment mechanism. The seal element may include an adhesive or fastener elements to adhere to the adjustment mechanism.

A first end of the cable may secure to the adjustment mechanism and a second end of the cable secures to the hinge of the orthopedic device. The adjustment mechanism is connected to the frame and is movable relative thereto on the basis of winding the cable and/or movement of the hinge. A guide is secured to the frame and orients the cable relative to the frame, the hinge and the adjustment mechanism. A segment of the cable may extend perpendicular to the frame between the adjustment mechanism and the guide.

A variety of configurations exist for mounting the cable to the brace and adjustment mechanism, often depending on the desired method of treatment. The configurations for mounting may likewise be arranged for tensioning the cable and/or applying a load on the anatomy of the wearer. For example, in a PCL brace, both ends of the cable may be fastened to a hinge or hinges (opposed sides) and the cable passes through the adjustment mechanism. Alternatively, in an ACL brace, both ends may be fastened to the frame and pass through the adjustment mechanism.

A method for operating a dynamic tension system includes regulating a cable by an adjustment mechanism connected to the cable arranged to incrementally wind or release said cable. The method involves engaging a tension control device, such as a torque-limiting tool, with the adjustment mechanism, winding the cable via the tension control device and the adjustment mechanism, and limiting winding of the cable from passing a predetermined tension level short of or fully winding the cable by the tension control device. The method may further include the step of mating a key of the tension control device with a keyhole of the adjustment mechanism, and then regulating the adjustment mechanism with the tension control device.

An orthopedic device may be provided including a frame, at least one hinge connected to the frame, a cable having a first end connecting to the at least one hinge and a second end, and an adjustment mechanism connected to the second end of the cable and arranged to incrementally wind or release the cable. The adjustment mechanism is connected to the frame and movable relative to the frame by articulation of the hinge and/or winding or unwinding of the cable. A tension control device, such as a torque-limiting tool, is arranged to limit the adjustment mechanism from winding of the cable past a predetermined tension level short of or fully winding the cable to inhibit overtensioning and/or applying an excessive load on the anatomy of the wearer.

Under another embodiment of the disclosure, the adjustment mechanism is integrally formed as part of the dynamic tension system. The adjustment mechanism includes a spool for retaining a cable, a shell for securing the brace to a wearer, and a knob for rotating the spool to regulate tension in the cable, wherein the adjustment knob further includes detent rods for limiting the torque needed to increase tension. A releasable locking element may also be provided for retaining tension in the cable. This arrangement allows the spool to turn with the knob so a clockwise rotation increases tension in cable, and a counterclockwise rotation decreases tension in the cable.

An advantage of the adjustment mechanism of the present disclosure is that it makes determining tension applied to a brace easier for a user since it automatically distributes a pre-determined tension to the cable. The user will know when the required initial loading has been reached by gauging when the knob slips over the spool during rotation. An audible click may be heard to alert the user that the initial torque limit has been exceeded. The placement of detent rods laterally inserted through the knob act to releasably engage the spool during rotation under a preset torque limit. This feature also prevents or reduces overtensioning the cable, which makes wearing the corresponding brace much more comfortable so as to minimize excessive loads on the anatomy of the wearer.

Under another embodiment, the adjustment mechanism can serve as a load-limiting clutch for external attachment to a dial-tensioning knob. The adjustment mechanism may include a top and bottom cap for sliding over the knob, wherein the bottom cap is fixedly secured to the knob and the top cap can be rotated relative to the bottom cap. Both the top and bottom cap may include a torque-limiting feature for helping control rotation of the knob. Another advantage of this embodiment is that the adjustment mechanism can be retrofitted onto existing dial-tensioning systems.

As the top cap is rotated, the bottom cap and knob are also rotated in unison. When the applied torque is less than a pre-determined value, the knob will continue to rotate in a clockwise direction and reel in cable to tighten a brace to a wearer. Once this pre-determined torque is exceeded, the top cap can continue to freely rotate without reeling in additional cable since the bottom cap and knob are prevented from rotating any further.

It should be appreciated that the torque-limiting feature employed by the top and bottom cap may include a variety of restrictive elements, such as a ball type detent, a flat band spring, or a tension coil spring. Each of these restrictive elements prevents the bottom cap from fixedly engaging with the top cap. This occurs when the top cap slips past corresponding engagement features on the bottom cap during rotation. It should further be appreciated that the desired initial torque limit can be adjusted by modifying many the restrictive elements, such as changing their shape or size.

All the embodiments above allow adjustment of tension at any position of extension or flexion.

BRIEF DESCRIPTION OF THE DRAWINGS

These and other features, aspects, and advantages of the present disclosure will become better understood with regard to the following description, appended claims, and accompanying drawings.

FIG. 9 is a detailed schematic view of a lower portion of the dynamic tension system including the adjustment mechanism and guide in the orthopedic device of FIG. 1a.

FIG. 18 is an exploded perspective view of another embodiment of an adjustment mechanism.

Figure 1A:
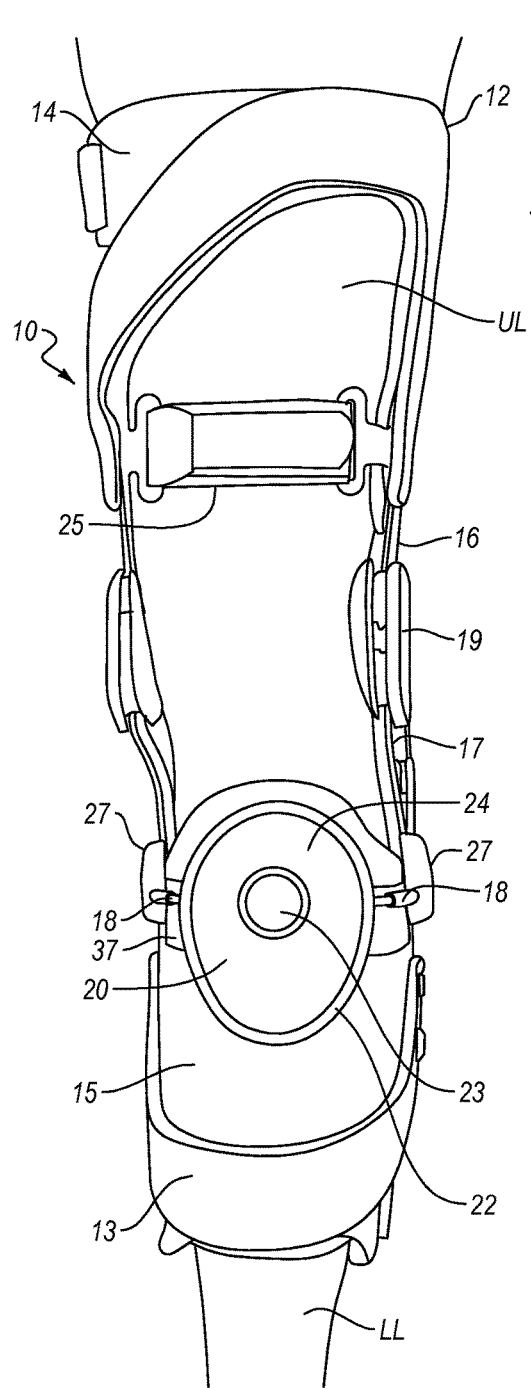
FIG. 1A is a rear perspective view of an orthopedic device utilizing a dynamic tension system according to an embodiment of a PCL brace.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of an orthopedic device having a dynamic tension system with various forms of adjustment mechanisms and the components thereof, and in no way limit the structures, configurations and components thereof according to the present disclosure.

DETAILED DESCRIPTION OF VARIOUS EMBODIMENTS

A. Overview

While the disclosure is susceptible to various modifications and alternative constructions, certain illustrative embodiments are shown in the drawings and are described below. It should be understood, however, there is no intention to limit the disclosure to the embodiments disclosed, but on the contrary, the intention is to cover all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning The adjustment mechanism described is configured for use with a dynamic tension system such as a dial-tensioning device used on an orthopedic brace. It should be remembered that the same concepts and methods described may be similarly employed for dynamic tension systems used on other orthopedic devices and are not limited solely to the anatomical locations discussed.

B. Embodiments of the Adjustment Mechanism

The following description refers to an adjustment mechanism configured for regulating the load imparted on a user by an orthopedic device. The features of this disclosure may apply to an adjustment mechanism for use with any orthopedic device that employs or requires tension dynamic tension system for securing the device to the body of the user. It should also be appreciated that the scope and aspects of the embodiments disclosed may apply to various other devices for which it is desirable to attach a tension dynamic tension system. In each disclosed embodiment, the dynamic tension system is connected to an orthopedic device so it maintains the full functionality of the orthopedic device.

Variants of a PCL brace or support that can include the adjustment mechanism can be found in U.S. patent application Ser. No. 13/644,824, filed Oct. 31, 2012, or variants of an anterior cruciate ligament (ACL) brace described in U.S. patent application Ser. No. 14/165,478, filed Jan. 27, 2014, each incorporated in their entirety by reference. A shear knob or torque-limiting tool, as described in U.S. provisional patent application No. 61/982,972, filed Apr. 23, 2014, described in U.S. patent application publication no. 2015/0053053, published on Feb. 26, 2015, may be used with certain embodiments requiring a torque-limiting tool and the application thereof is incorporated in its entirety by reference.

Figure 1B:
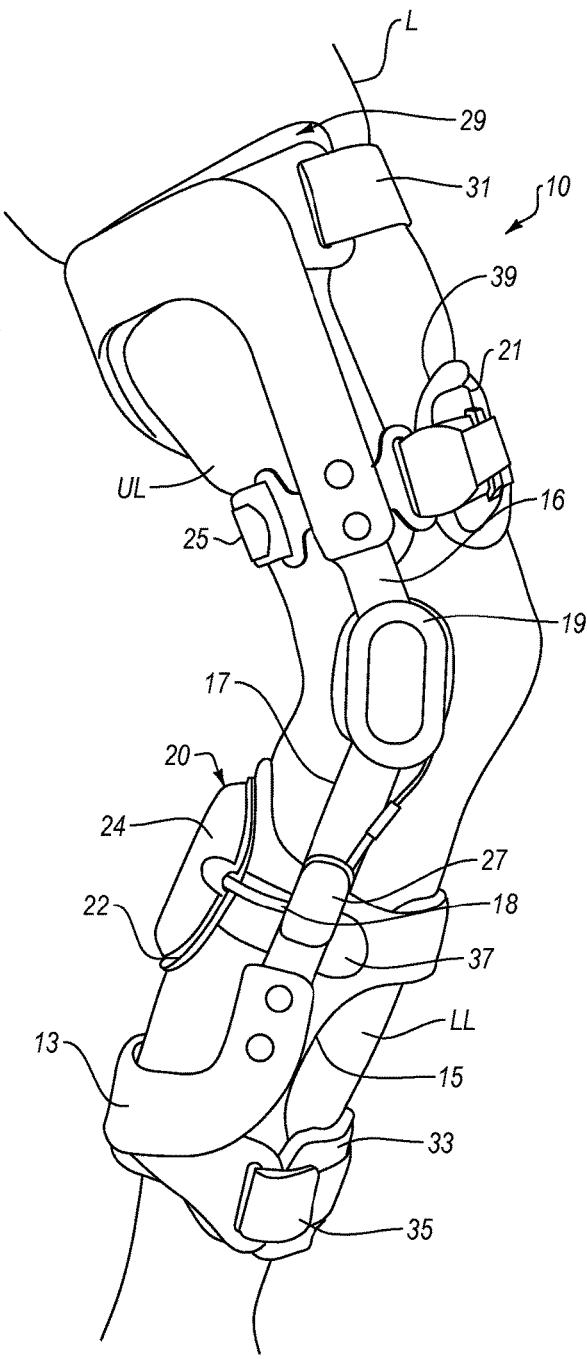
FIG. 1B is a side perspective view of the orthopedic device of FIG. 1A.

Referring to FIGS. 1A and 1B, an orthopedic device is shown in a PCL knee brace 10 securable to a leg and that includes an improved adjustment mechanism 24 according to an embodiment of the present disclosure. The brace 10 further includes a frame having an upper frame element 12 secured to an upper leg UL and a lower frame element 13 secured to a lower leg LL. The upper and lower frame elements 12, 13 are spaced apart from and connected to a hinge assembly 19 at the knee K by the upper and lower struts 16, 17. In a variant of a PCL brace, both the upper and lower frame elements 12, 13 are arranged on the posterior side of the device for fitting on a wearer's upper and lower leg, respectively. Padding 29 may be secured along the surface of the upper and lower frame elements 12, 13. A dynamic tension system 20 is used to urge a force against the leg L of a wearer of the brace 10.

An upper thigh shell 14 extends from the upper frame element 12 and a strap 31 secures to the upper thigh shell 14 and the upper frame element for securing the brace to a wearer's leg. A femoral shell 21 secures to an anterior side of the wearer's upper leg or thigh and a proximal-anterior strap 39 secures the femoral shell 21 to opposed sides of the upper frame element 12 or the upper struts 16. A proximal-posterior strap 25 is located opposite the proximal-anterior strap 39 and secures to the upper frame element 12 or the upper struts 16.

An anti-migration wrap 15 carries the dynamic tension system 20 and connects to the lower frame element 13 or the lower strut 17 by a strap and a bracket, such as a D-ring, as shown in U.S. patent application Ser. No. 13/644,824. The wrap 15 may be adjustable and tightenable over the lower leg, and may be integrally connected between the locations corresponding to the dynamic tension system 20 and the lower frame element 13. A tibial shell 33 connects to a strap 35 and secures to the lower frame element 13, as described in U.S. patent application Ser. No. 13/644,824.

The dynamic tension system 20 includes a base 22, which carries a dynamic tension system 24 and is supported by the wrap 15. The dynamic tension system 20 is positioned over the upper and fleshy portion of a wearer's posterior calf. The dynamic tension system 24 serves as a tightening device and includes a tensioning element 18 such as a cable.

When the brace is arranged in extension, a cable 18 extends from the dynamic tension system 20 in a lateral direction toward the lower strut 17 by extending through a first set of guides on the shell 22, and is redirected in a longitudinal direction by a second set of guides 27 on the lower strut 17 to an aperture on a cover of the hinge 19. The wrap 15 may include a guard 37, with a more durable material than a textile, foam, or other material used to make the guard 37, to avoid wear of the wrap 15 as the cable 18 adjusts or moves.

It is preferable that the cable 18 is arranged laterally relative to the lower strut 17 and may be received by the second set of guides 27 on the lower strut 17. Both sets of guides may comprise tubes, brackets, channels and any other form that will permit the cable to be directed in a straight orientation with the first set of guides, and a curved or reoriented orientation with the second set of guides 27. The second set of guides 27 may be located on the struts for routing the cable in a direction perpendicular to the first set of guides.

The cable may be attached at an end to the adjustment mechanism, or the cable may pass entirely through the adjustment mechanism while being capable of being wound about the spool, and its end portions being secured to the orthopedic device such as along a frame portion, hinge, or other suitable location depending on the application.

While the embodiment of FIG. 1 shows the cable 18 running alongside an anterior side of the lower strut 17 as it approaches the hinge 19 additional guides may be employed along the lower strut to maintain the cable in this orientation, or in an alternative orientation. The arrangement of the dynamic tension system is not limited to the configuration in FIGS. 1A and 1B, but a variety of configurations and reversal or modification of the features and is envisioned, as shown in U.S. patent application Ser. No. 14/165,478.

Figure 2:
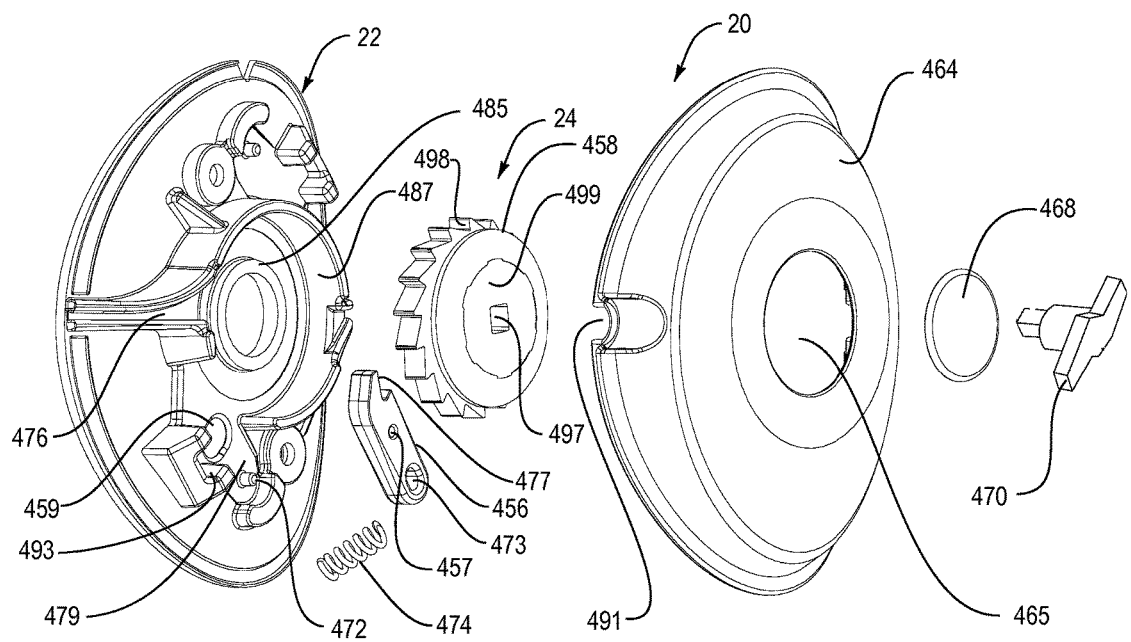
FIG. 2 is an exploded view of the adjustment mechanism of the dynamic tension system of FIG. 1A.
Figure 3:
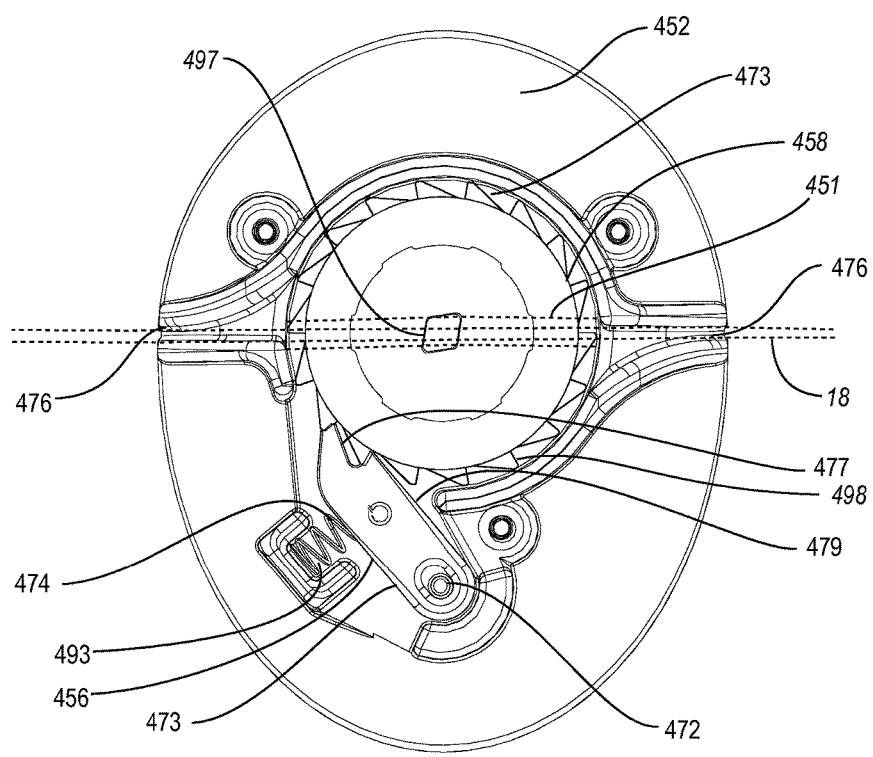
FIG. 3 is a plan view of the adjustment mechanism of FIG. 2 without the shroud.

FIGS. 2 and 3 show a detailed version of the dynamic tension system 20 including the adjustment mechanism 24 having the shell 22, a shroud 464 and a cover 468 for covering a hole 465 defined by the shroud 464. In a variation, the cover 468 may only cover a keyhole formed by adjustment mechanism, such as the spool, or it may be arranged to cover a broader area. A torque-limiting tool 470 may be provided for regulating the adjustment mechanism 24 and limiting tension of the cable.

The base 22 and the shroud 464 define channels 476 formed on opposed sides thereof for directing the cable received and adjusted by the adjustment mechanism 24. The shroud 464 also defines recesses 491 proximate the channels 476 for permitting outward movement of the cable 18. The adjustment mechanism 24 includes a spool 458 arranged to wind the cable 18 and defines a plurality of teeth 498 about a periphery thereof. A pawl 456 is pivotally arranged to engage the plurality of teeth 498 by a detent 477 formed at first end. The base 22 retains the spool 458 arranged to rotate relative to the base 22. The pawl 456 is pivotally mounted to the base 22. In this embodiment, as shown in FIG. 3, the cable 18 passes through the adjustment mechanism via a channel 451 formed by the spool 458 and is appropriately wound about the spool 458, with end portions of the cable secured to the hinges.

An access 459 is formed by an opening defined by the shell 22 and provides communication from exterior of the base 22 into the adjustment mechanism 24 for disengaging the pawl 456 from the spool 458. The pawl 456 defines an access feature 457, such as an aperture, for enabling movement of the pawl 456 from the spool 458 via the access 459. A screwdriver or similarly pointed device may be inserted through the access 459 to engage the access feature 457 and move the pawl 456 against the compressive force of the spring 474 to permit the spool 458 to rotate freely, loosening the tension of the cable. The access 459 is preferably made difficult or at least concealed from easy use to prevent users from loosening tension without supervision or guidance from a clinician.

The base 22 defines a cavity 487 arranged for retaining the spool 458 and has a profile accommodating a shape of the spool 458. The base 22 defines a boss 485 about which the spool 458 rotates. The base 22 defines a pin 472 over which an aperture 473 at a first end of the pawl 456 fits so the pawl 456 pivots so an opposed second end of the pawl 456 carrying the detent 477 can engage or disengage from the plurality of teeth 498. The base 22 defines an enclosure 493 arranged to receive and retain the first end of the spring 474, and an enclosure 479 for permitting pivoting of the pawl 456.

A tension control device 470 may be the torque-limiting tool 470 arranged to fail upon reaching the predetermined level of tension in the cable in that tension in winding at the predetermined level of tension causes the torque-limiting tool to fail. The torque-limiting tool is described in fuller detail in U.S. patent application No. 61/982,972. The torque-limiting tool 470 has a key part 471 and a handle 489 arranged to shear from the key part 471 at a predetermined load such that upon reaching the predetermined tension level in the cable the torque-limiting tool fails by the handle 489 shearing apart from the key part 471. The shroud 464 is arranged to cover the adjustment mechanism 24, and has an opening 465 arranged for providing access to the adjustment mechanism 24. The tension control device 470 is adapted to extend through the opening 465 to engage the adjustment mechanism 24 through keyhole 497 and selectively rotate the spool 458. A plate 468 is arranged to selectively secure over the opening 497 and covers a face 499 of the spool 458 to prevent access to the adjustment mechanism 24.

Figure 4:
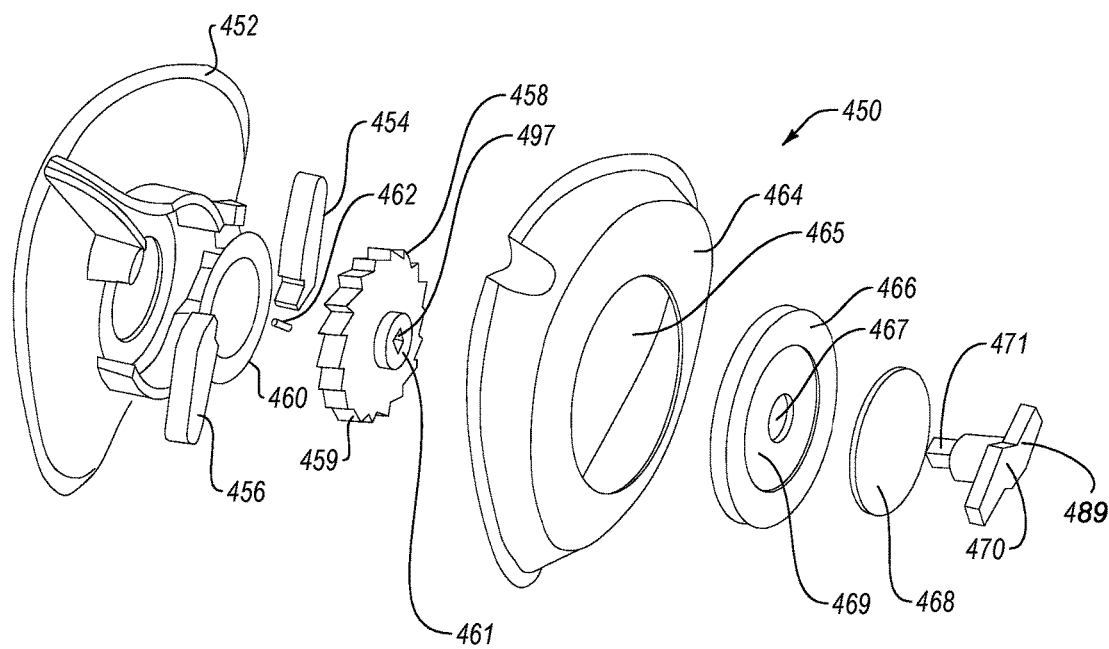
FIG. 4 is a variation of the adjustment mechanism of FIG. 2 and further shows a shear knob.

The torque-limiting tool 470 having a key part 471, as shown in FIG. 4, arranged to be received and engages a keyhole 497 defined along the face of the spool 458 for winding of the cable 18. The key part and keyhole 471, 497 may have a variety of matching shapes, from complex to simple. Preferably the shapes are arranged to prevent a user from adjusting the tension in the cable without supervision or action by the clinician.

In the initial brace application, the straps and wrap are unfastened, and the hinges may be adjusted to have range of motion adjustment. A leg L of the user is placed in full extension with the hinge preferably slightly above the knee K joint line so the brace can properly seat itself. The wrap and straps are then fastened about the user's upper and lower leg UL, LL.

Various torque-limiting tools are provided according the desired maximum tension in the cable. With the user in a standing position and the leg L in full extension, the desired torque-limiting tool engages the adjustment mechanism with the plate removed so access to the adjustment mechanism is possible through the opening in the shroud. The clinician slowly turns the torque-limiting tool in a direction until the torque-limiting tool fails or prior to failure. The torque-limiting tool is removed and the plate is installed over the opening in 24. A sticker or other prevention element may be used to secure over the keyhole of the spool to prevent a user from tampering with the keyhole to adjust the adjustment mechanism.

Figure 16:
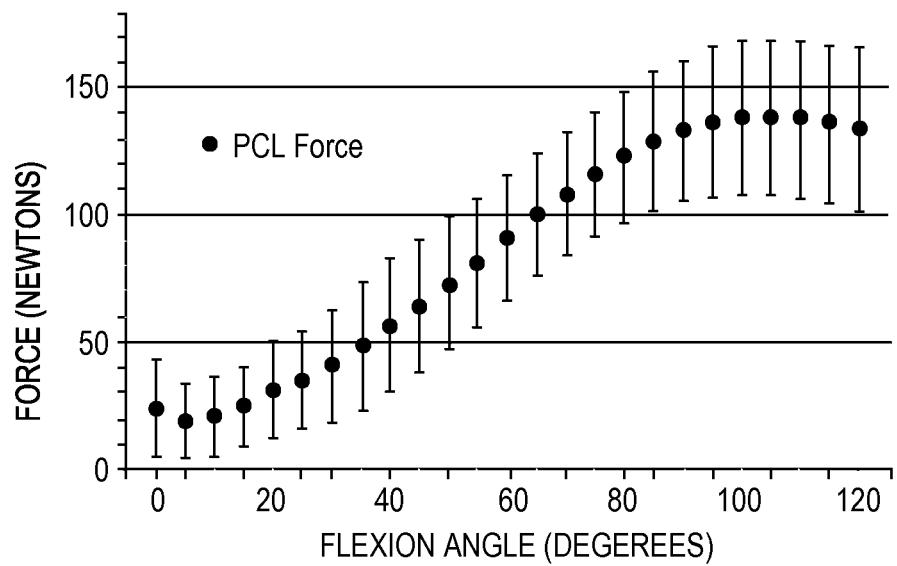
FIG. 16 is a graphical representation of the tension in the PCL.
Figure 17:
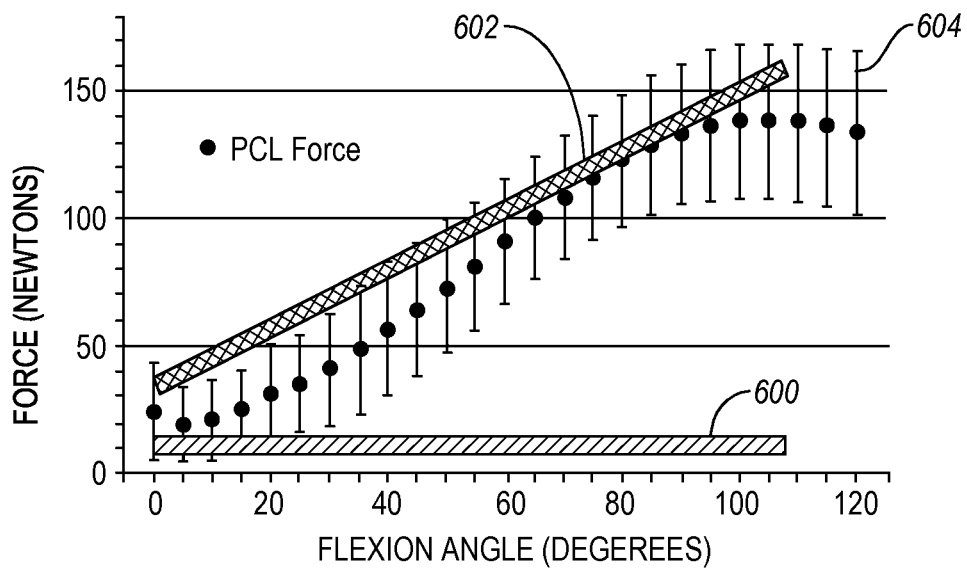
FIG. 17 is a graphical representation of FIG. 16 overlaid with a constant force and against a prior art device.

As an alternative to placing the leg L in full extension, a clinician may apply a maximum tension in the cable when the wearer places the leg in flexion, generally at 90 degrees. In this manner, the cable is tensioned at the high end of the slope, as depicted in FIGS. 16 and 17 and set at a highest load rather than a lowest load. The torque-limiting tool may be arranged to the maximum load at the high end of the slope of load versus flexion angle.

As an alternative to using a torque-limiting tool, a clinician may arrange the length of the cable so a maximum tensioning or winding of the cable corresponds to a desired maximum load.

If it is desired to re-tension the dynamic tension system, the brace is removed from the user. The dynamic tension system is removed from the wrap and the dynamic tension system is flipped over to expose its underside. A tool is inserted into the access of the base and the access element of the pawl, and a force is applied to disengage the pawl from the spool. While the pawl is disengaged from the spool, the cable is pulled out from the adjustment system which causes the cable to unwind and the spool to spin. Once the cable is loosened, the clinician restarts the same method used for installing the brace and setting the tension in the cable.

FIG. 4 shows another embodiment of an adjustment mechanism 450. According to this embodiment, there is a dynamic frame element 452, and a pair of opposing pawls 454, 456 engageable with a plurality of teeth 498 formed about a spool 458. Rather than linearly engaging the teeth 498, the pawls 454, 456 are arranged for rotating into the teeth 498, and are arranged to pivot at pivot points 472 defined in combination with the interior cavity of the dynamic frame element 452. A cable (not shown) extends about the spool 458 and channels 476 formed on opposed sides of the shroud 464. A spring 462 may be provided in combination with one or both of the pawls 454, 456. The pawls 454, 456 are preferably spring loaded by a spring 462 biased between a boss 485 formed by the interior of the dynamic frame element 452 and the pawl 454, 456.

A washer 460 is provided between the dynamic frame element 452 and the spool 458. The spool 458 has an aperture 461 arranged for connecting to the key 471. The key 471 is arranged to extend through the shroud 464 and the cap 466 adapted to engage the spool 458 and fill the opening 465 defined by the shroud 464. The cap 466 defines a hole 467 arranged to permit a locking end of the key 471 to extend freely therethrough and freely rotate therein. When the key 471 is not being used, a cover 468 is received by a recess 469 formed by the cap 466 and covers the hole 467.

Figure 5:
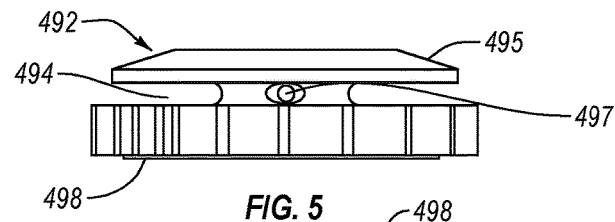
FIG. 5 is an elevational view of another embodiment of a spool for use in the adjustment mechanism of FIG. 2.
Figure 6:
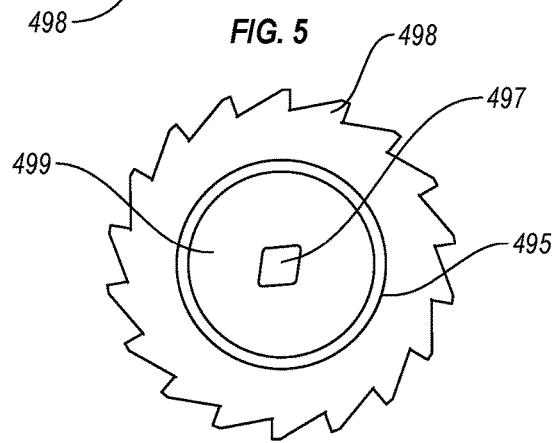
FIG. 6 is a bottom plan view of the spool of FIG. 5.

FIGS. 5 and 6 show another spool embodiment wherein the spool 492 defines circular stem 494 forming a recess by spacing apart a cap 495 and gear teeth 498 so the spool 492 is a single unit. The recess is adapted to receive a cable, which wraps around the stem 494. The cable can be secured to the spool 492 by securing to the stem 494 through the aperture 497 formed on the stem 494. The spool 492 has a cavity 499 that can receive a portion of the cable, and an aperture or keyhole 497 for tensioning the cable, as discussed in the foregoing. Alternatively, the cable may pass completely through cavity and the ends of the cable are secured to the hinges or frame rather than an end being secured to the spool itself.

Figure 7:
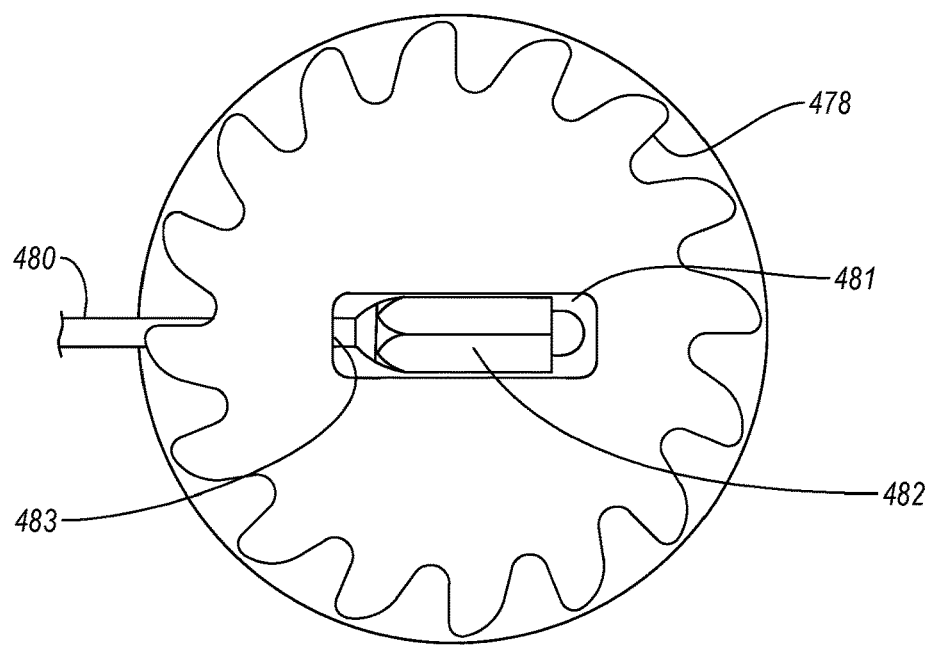
FIG. 7 is a variation of the spool in FIG. 5.
Figure 8:
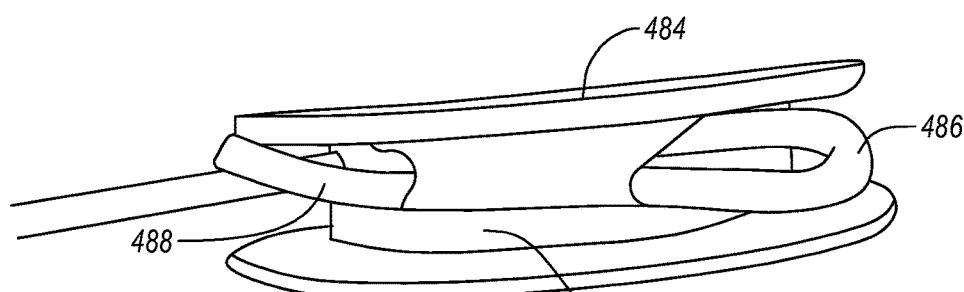
FIG. 8 is another variation of the spool of FIG. 5.

FIG. 7 displays a spool embodiment 478 arranged to receive an end of the cable 480. The spool 478 defines an elongate recess 481 through which an end of the cable 480 extends from a channel 483 formed from spool 478. A tab or ferrule 482 may be press fit onto the end of the cable 480 to retain the cable end within the recess 481. The ferrule may be clamped centered on the cable. The tab or ferrule 482 is preferably sized and configured to closely fit within the recess to be lodged and contained within the recess. While FIG. 7 only shows one recess, there may be two recesses juxtaposed from one another, with opposed channels formed by the spool to accommodate two cables or a single cable passing through the spool FIG. 8 shows another embodiment wherein the spool 484 defines first and second channels 490 but not limited to being parallel to one another. An end portion of the cable 486 extends through the first channel 490 and loops back into the other channel 490 bending the cable so the end 488 of the cable returns generally at an entrance of the first channel. The configuration of the cable bends the cable to prevent the end from slipping through the channels, and secures the cable to the spool.

Figure 9:
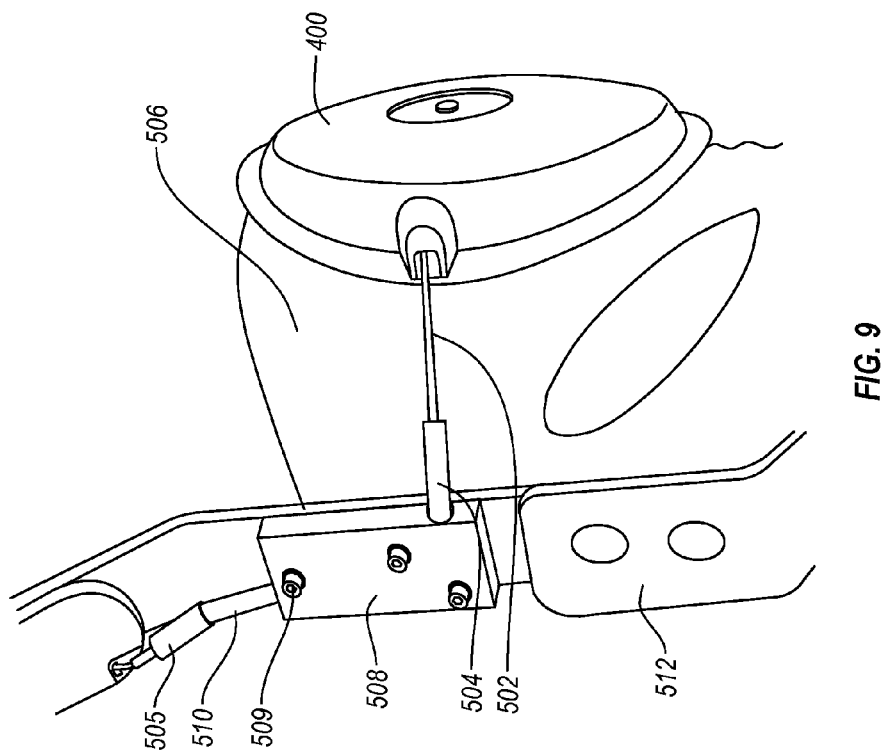

FIG. 9 illustrates the adjustment mechanism 400 secured onto a knee brace frame 512. The adjustment mechanism 400 is mounted on a flexible support 506 securing to the knee brace frame 512. The flexible support 506 may be a soft-good support with padding characteristics providing a comfort interface between the wearer and the adjustment mechanism. Cables 502 extend from both sides of the adjustment mechanism 400 and extend to guide 508 that direct the cable upwardly toward the brace hinge. To protect the cable 502, a ferrule or other guard 504 secures to the cable and a sheathing 510 covers portions of the cable 502.

Figure 10:
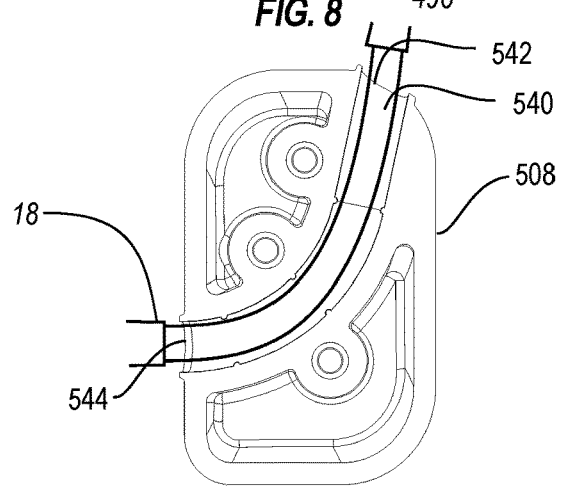
FIG. 10 is a detailed view of an inside surface of the guide in FIG. 9.

FIG. 10 shows the guide 508 as being a plate having a channel 540, which guides the cable 502 in a direction through ends 542, 544. As exemplified in FIG. 9, pins 509 may place the cable in the correct or desirable orientation. Ferrules or sheaths 504, 505 may be placed both before the guide 508 and hinge (not shown) to protect from wear. The sheaths 510 may be sized so they will always take up portions of the cable and fixed in length between the various components of the dynamic tension system.

Figure 11:
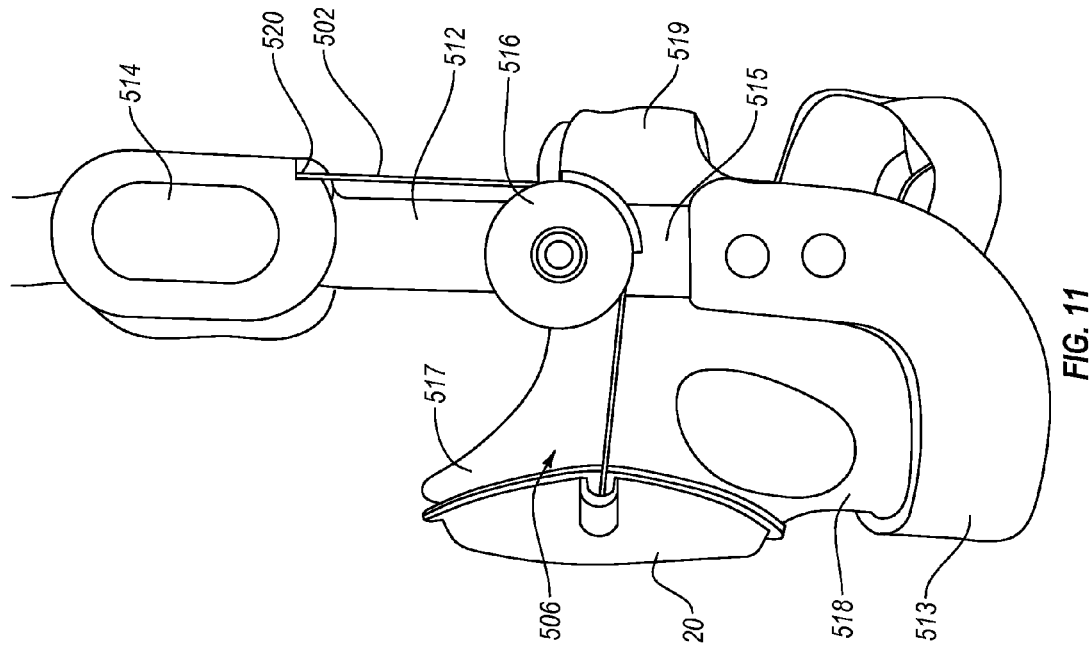
FIG. 11 is a detailed schematic view of a variation of the guide in FIG. 9 on a frame of the orthopedic device of FIG. 1A.

FIG. 11 shows another embodiment wherein the guides are formed by pulleys 516 mounted onto the knee brace frame 512. In this embodiment, the cable is shown without the sheathing and/or ferrules, but the cables can be provided with the sheathing and ferrules, as described above.

The flexible support 506 may be formed to include a posterior main portion 517 adapted to extend beyond the footprint of the dynamic tension system 20. The flexible support 506 includes a lower portion 518 extending downwardly toward a lower portion 513 of the frame 512, and a side strap portion 519 extending to lateral and medial portions 515 of the frame 512 and extending to form a strap so the flexible support 506 circumferentially fits about the leg of the wearer. The side strap portion 519 may secure to the frame 512 at the lateral and medial portions 515, or may be only attached at the lower frame portion. The flexible support 506 may also extend along the lower frame 513 to provide addition padding to compensate for the force urged against the leg by the dynamic tension system 20.

Figure 12:
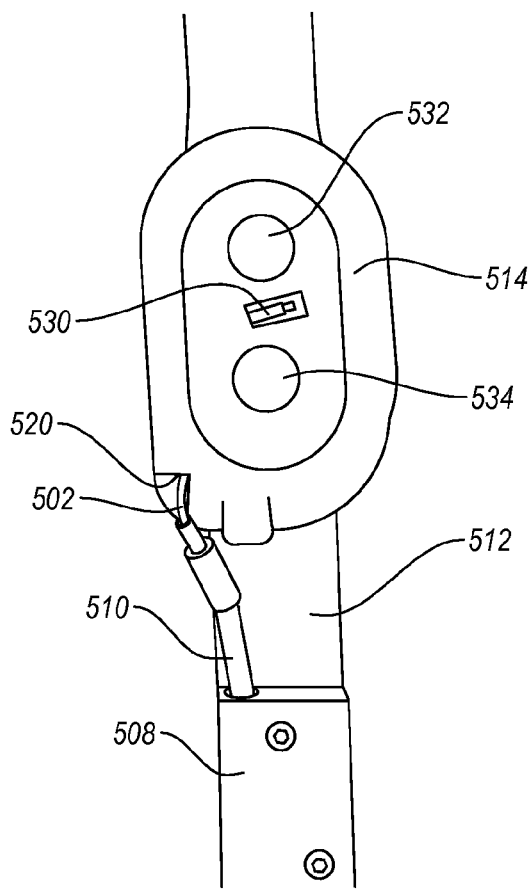
FIG. 12 is a side schematic view of an upper portion of the dynamic tension system including a hinge plate and the guide in the orthopedic device of FIG. 1A.
Figure 13:
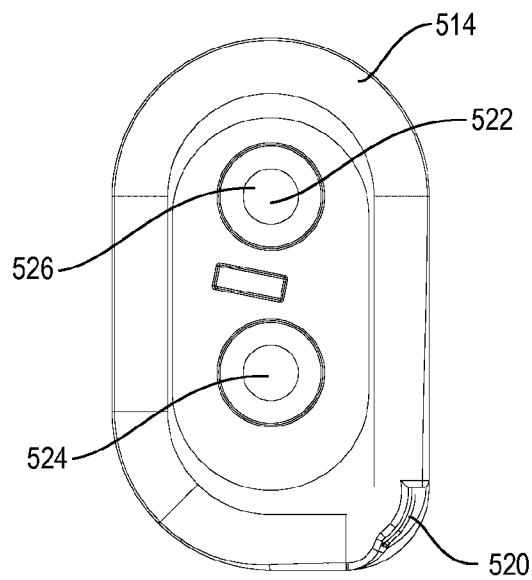
FIG. 13 is an outside elevational view of a hinge plate used in the embodiment of FIG. 12.
Figure 14:
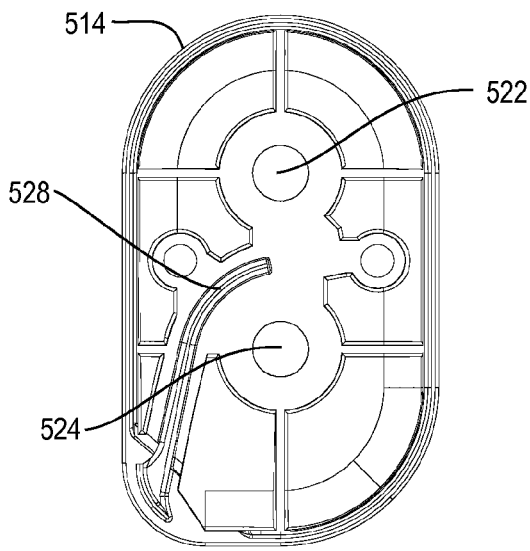
FIG. 14 is an inside elevational view of the hinge plate of FIG. 13.

FIGS. 12-14 show a hinge plate 514 depicted in FIG. 11. The hinge plate 514 includes an opening 520 for receiving the cable 502. The hinge plate 514 includes openings 522, 524 for receiving pins 532, 534 belonging to the hinge. A slot 526 is used to receive an anchored portion 530 of the cable 502, which extends through and outwardly of the hinge plate 514. On the interior of the hinge plate 514, the cable 502 extends through an opening 520 formed at the base of the hinge plate 514 and through a channel 528 defined along the interior surface of the hinge plate 514 to guide the cable in a desired orientation relative to the openings 522, 524.

Figure 15:
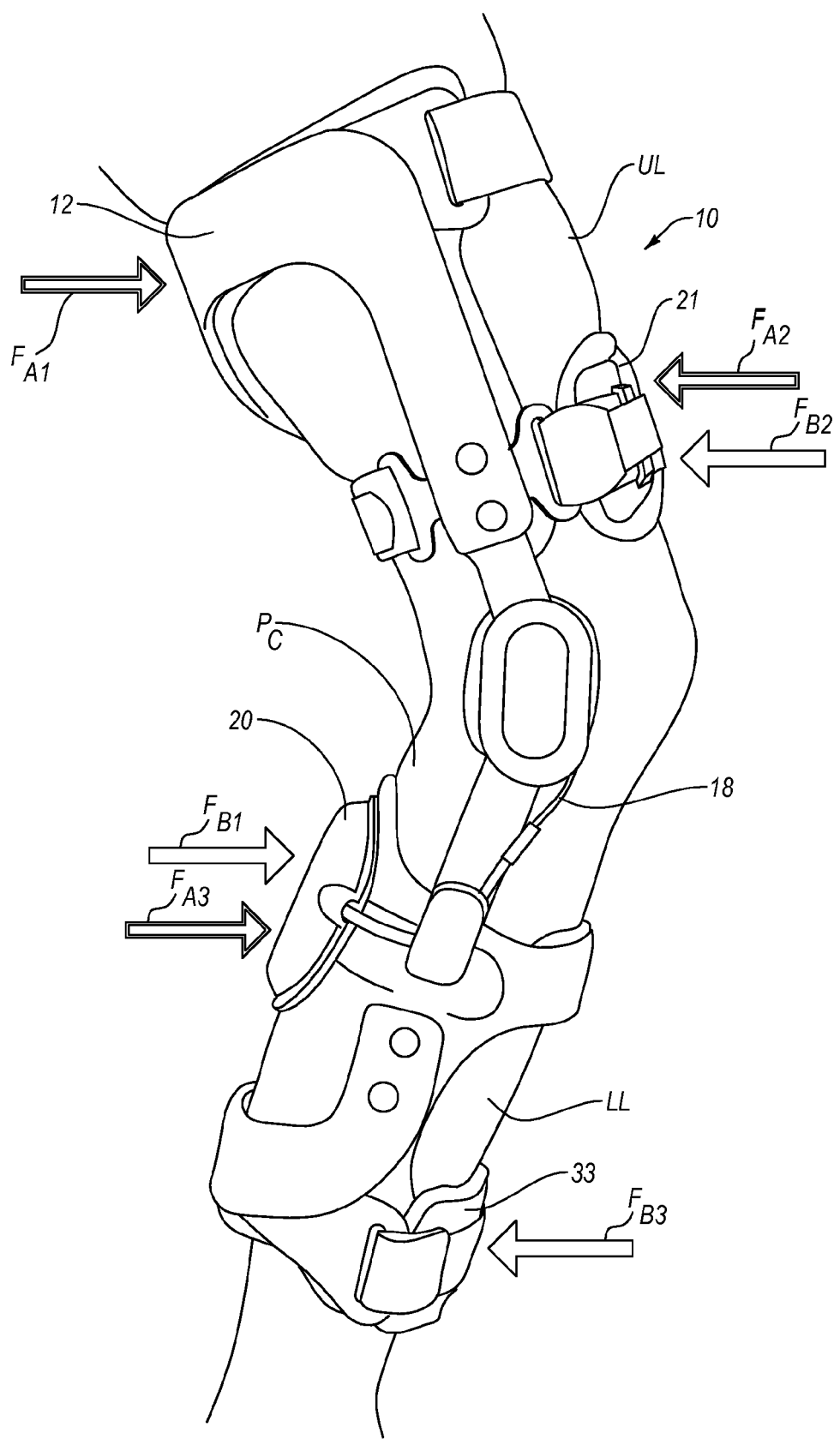
FIG. 15 is a schematic view showing how the orthopedic device and dynamic tension system of FIG. 1A dynamically applies loads.

Referring to FIG. 15, the orthopedic device 10 is a PCL brace arranged to dynamically load the posterior calf $P_c$ to reduce the load on the PCL. There is a dual 3-point system used to counterbalance the forces on the leg. The first system includes a force $F_{A1}$ applied by the upper frame 12 and a force $F_{A3}$ the dynamic tension system 20 and a force $F_{A2}$ counteracted by the femoral shell 21. The second system includes a force $F_{B1}$ exerted by the dynamic tension system 20 and counteracted by a force $F_{B2}$ exerted by the femoral shell 21 and a force $F_{B3}$ from the tibial shell 33.

FIGS. 16 and 17 exemplify how the dynamic tension system exerts a load over flexion angles to the calf by the brace, which correlates to linear displacement of the tibia relative to the femur used to provide PCL stability. These graphs are derived from research related to the following publications, "A Historical Perspective of PCL Bracing," Knee Surg. Sports Traumatol Arthrosc., DOI 10.1007/s00167-012-2048-9, Epub. 24 May 2012, and "Functional Bracing of ACL Injuries: Current State and Future Directions," Knee Surg. Sports Traumatol Arthrosc., 2014 May 22(5):1131-41. DOI: 10.1007/s00167-013-2514-z. Epub 2013 Apr. 27.

FIG. 16 shows how as a user goes into 90 degrees flexion, the load will increase to approximately 140 N. The PCL experiences variable tensile forces during knee flexion and the brace applies correct anatomic joint forces that vary with knee flexion angle, as shown in FIG. 17 by a natural linear line 602 and line 604 shows how the PCL brace compensates for natural requirement of variable forces. Line 600 shows the impact of a commercially available brace wherein the force remains constant during flexion, and therefore does not compensate for variable forces as in the embodiments of the disclosure.

Figure 20:
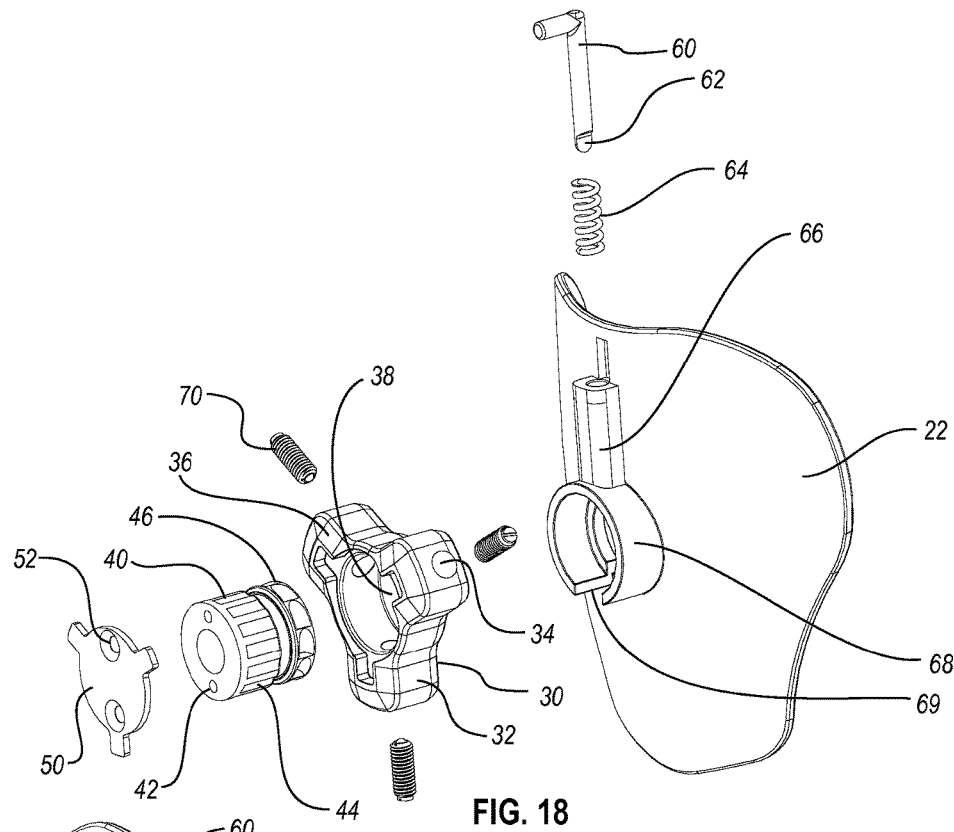
FIG. 20 a cross-sectional view taken along line XX-XX in FIG. 19.
Figure 19:
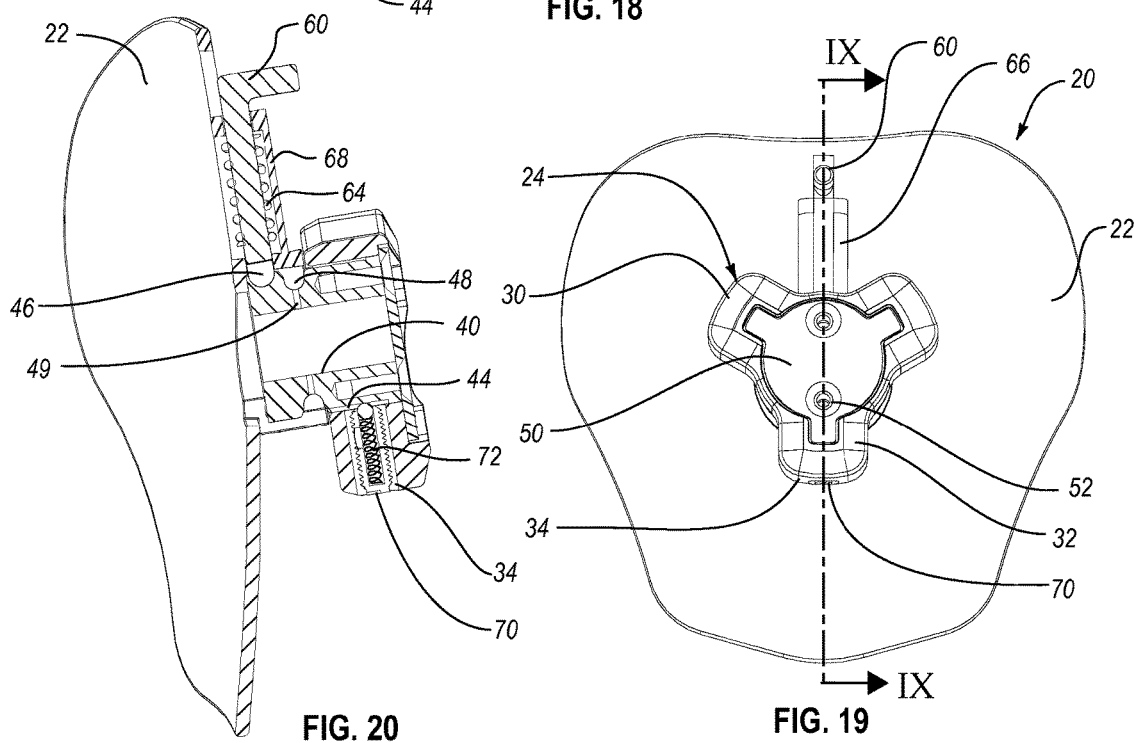
FIG. 19 is a front elevational view of the adjustment mechanism of FIG. 18.

Referring to FIGS. 18-20, another embodiment of the dynamic tension system 20 is shown in more detail. In particular, the dynamic tension system includes a spool 40 configured for retaining a tensioning element 18 such as a cable, a base 22 with a spool housing 68 for receiving the spool, an adjustment knob 30 for rotating the spool to regulate tension in the cable, and a releasable locking element 60 configured to prevent an unwanted decrease in cable tension. The spool housing 68 is preferably at the center of the shell 22, and includes a C-shaped circular wall protruding from the curved outer surface of the shell to define a hollow cavity configured to receive at least a distal end of the spool 40. The open end of the C-shaped wall is pointed downward allowing the cable 18 to extend from the spool 40 to the brace frame.

The spool 40 is tubular-shaped and sized to fit in the spool housing 68. The spool 40 has an upper portion at its proximal end having detent notches 44 equally spaced along an outer periphery. The spool further includes a lower portion at its distal end having equally spaced alcoves 46 along an outer periphery for engaging the locking element 60. When the spool 40 is received in the housing 68, it can be rotated either clockwise or counter-clockwise to shorten or lengthen the cable, respectively. The locking element 60 is arranged so the spool 40 can be freely rotated clockwise to apply tension to the cable. When rotation is stopped, the locking element 60 automatically engages the spool 40 to prevent counter-clockwise rotation maintaining the current tension in the cable. The direction is not limited to the directions described herein but may arranged in a variety of different directions.

The locking element 60 is preferably a retractable plunger such as a pin having a distal end 62 that includes a flange flat on one surface and dome-shaped on its opposite surface. The plunger 60 is inserted into a first end of a locking guide 66 defining a through-channel on the outer surface of the shell 22. A second end of the locking guide 66 defines a second opening through a portion of the C-shaped wall of the spool housing 68. An elastic member 64, such as a coil spring, is preferably located inside the channel for urging the plunger 60 toward the spool 40.

Each alcove 46 on the spool may be shaped so the distal end 62 of the plunger fits snugly inside. Further, each alcove includes a flat side wall for engaging the flat portion of the flange at the distal end 62 of the plunger, and a concave cavity for accommodating the dome-shaped portion. As the spool 40 is rotated clockwise, the curved surface of the dome-shaped portion at the distal end 62 of the plunger 60 slides against the corresponding curved interior surface of the dome-shaped portion of the alcove to consequently force the plunger out of the alcove. As the spool 40 is continually rotated clockwise, subsequent adjacent alcoves become aligned with the locking guide 66 and the coil spring 64 automatically forces the plunger to drop back down for locking engagement in the reverse direction.

When the retractable plunger 60 is in its locked position, the position of the spool 40 remains locked, but the user can still rotate the spool clockwise if desired. In order to manually rotate the spool counter-clockwise, the locking element 60 must be retractable so a user can first manually pull the plunger out of engagement with the spool. To make accomplishing this easier, the plunger 60 preferably includes a handle at its proximal end that the user can grip to pull it through the channel of the locking guide 66 in the direction away from the spool 40. To properly disengage the plunger from the spool, the locking force of the spring 64 must be overcome. Unlocking the spool 40 allows it to be unwound in a counter-clockwise direction so tension in the cable can be decreased. Once the plunger 60 is retracted and the cable 18 is loosened, the brace can be easily doffed. It will be noted that it is not required to loosen tension to doff the brace, but that the plunger can be released so the brace can be retensioned.

A knob 30 can be attached to the proximal end of the spool 40 in order to easily rotate it within the spool housing 68. The knob 30 has a hollow cylindrical core 38 for receiving the spool 40. The knob can be shaped to include equally spaced grips 32, wherein each grip has a threaded hole 34 for receiving a threaded detent rod 70. Turning briefly to FIG. 20 each detent rod 70 includes a hollow shaft having a spring 72 loaded detent ball 74 within. Laterally inserting each detent rod 70 through the knob 30 allows the knob to releasably engage the spool during rotation under a preset torque limit. When the knob is attached to the spool 40, the detent balls 74 lock into a corresponding detent notch 44 on the spool so the spool turns with the knob.

During operation of the adjustment mechanism 24, the knob 30 is used to turn the spool, which winds the cable 18. Once the cable 18 is tightened to a desired tension, sustained turning of the knob 30 causes it to slip on the spool 40 preventing further winding of the cable. This results from the spring loaded detent balls' 74 inability to lock into adjacent detent notches 44 as the knob is turned. When this happens, an audible click may be heard as the detent balls 74 slide across each detent notch 44, which helps the user know when the initial tension load is met. The resistance applied by the locking element 60 is much higher than the torque exerted by the knob 30.

The placement of each detent rod 70 within a corresponding threaded hole 34 is adjustable. This allows the desired maximum load to be set by retracting or extending each detent rod 70 either away from or closer to the spool 40, respectively. Further, the desired maximum load can be readjusted by altering the placement of each detent rod 70 as just described.

A recess 36 on the top surface of the knob 30 is adapted to engage a lock plate 50, which serves as a top cover for securing the spool 40 within the knob. In particular, the lock plate 50 includes at least one hole 52 for receiving a fastener, such as a screw. At least one corresponding threaded engagement hole 42 on the top surface of the proximal portion of the spool 40 is provided for securing the fastener so the lock plate, spool and knob all fit together. at least one hole 52 in the lock plate 50 is preferably chamfered so a screw head will remain flush with the surface of the lock plate and not protrude to potentially snag onto foreign objects during use.

FIG. 20: A concave circular groove forms a neck 48 between the upper and lower portions of the spool 40, which retains the cable 18 as it is wound and/or unwound. A pair of apertures 49 on opposite sides of the neck 48 secures the cable to the spool. As the spool 40 is rotated by the knob 30, a clicking sound is made by the retractable plunger 60 every time it snaps into to an adjacent alcove 46 to alert the user about how much cable has been wound. The detent may be arranged to provide notification that the maximum tension has been reached, or may be provided without such an audible sound.

Figure 21:
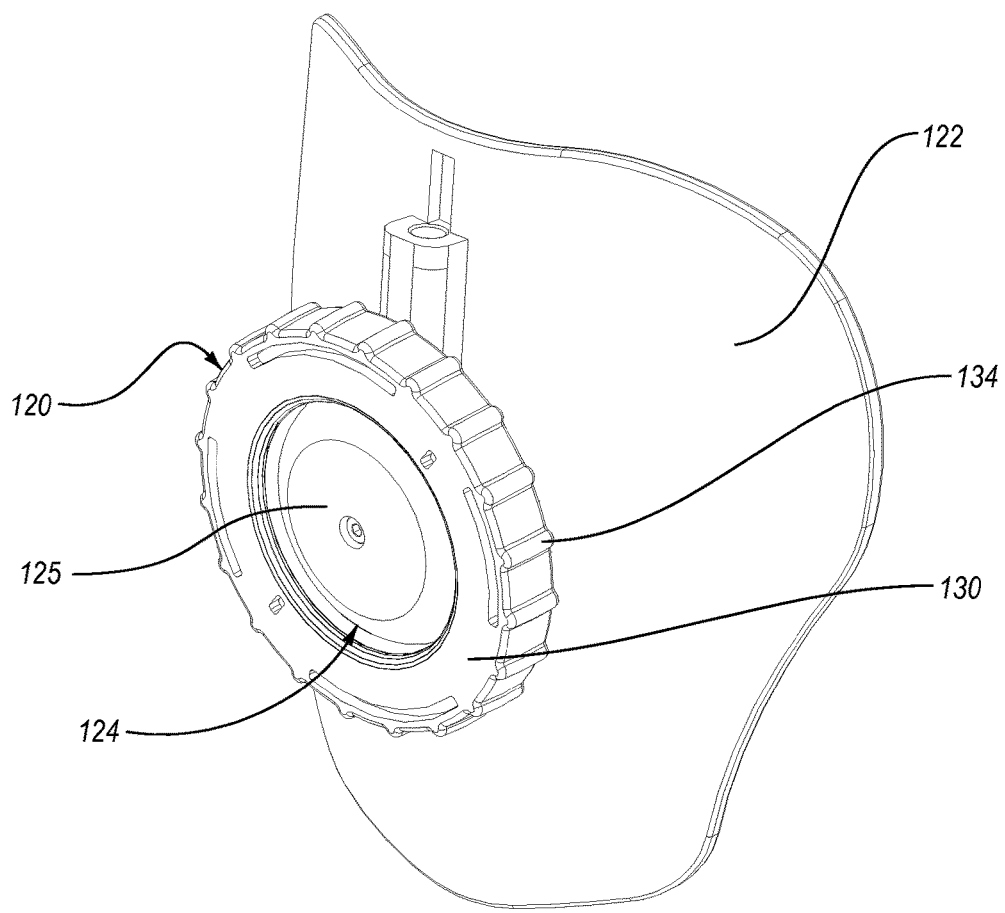
FIG. 21 is a perspective view of an embodiment of the adjustment mechanism.

In another exemplary embodiment in FIG. 21, an adjustment mechanism 120 can be configured to act as a load-limiting clutch for attachment to a separate dynamic tension system 124. The dynamic tension system 124 is again a dial-tensioning device that includes a tensioning element as shown in other embodiments, such as a cable. This adjustment device 124 may be provided by BOA Technology Inc., and is also described in US 2009/0287128, which is incorporated by reference. The tensioning element is secured to the dial-tensioning device 124 in a manner such that its length can be adjusted according to a desired incremental and preselected adjustment to its tension.

The dial-tensioning device 124 may be rotated clockwise to decrease the length of the tensioning element and increase its overall tension. To decrease the cable's overall tension, the dial-tensioning device 124 may be rotated counterclockwise to increase the length of the cable 18. The base 122 can be slidingly and pivotally secured to the lower struts, as shown in FIGS. 1A and 1B. As the dial-tensioning device 124 is regulated to adjust the tension in the tensioning element, the base is urged toward the wearer's lower leg moving closer to the lower struts. The base 122 can also pivot relative to the lower struts 117 to accommodate flexion of the knee and leg.

The dial-tensioning device 124 is preferably centrally secured to the frontal or outer surface of the base 122, and the tensioning element extends from both lateral and medial sides of the dial-tensioning device to the lower strut segments. The base 122 may include a first set of guides that maintain the direction of the tensioning element toward the lower strut segments. The tensioning element is received on the lower strut segments by a second set of guides which direct the tensioning element toward the hinge assembly, as in FIGS. 1A and 1B.

Ends of the tensioning element are preferably retained within the dial-tensioning device 124 and the portion of the cable outside the dial-tensioning device extends continuously toward the hinge assembly 19 without interruption. While this is the preferred embodiment, it will be noted that the orthopedic device is not limited to a single cable or a single dial tensioner, but it is envisioned that multiple cables and dial tensioners may urge or move corresponding base relative to the brace.

The adjustment mechanism 120 fits over and is secured to the dial-tensioning device 124 on the base 122. In this arrangement, the adjustment mechanism 120 can help control the torque applied to a dial-tensioning knob 125.

Figure 22:
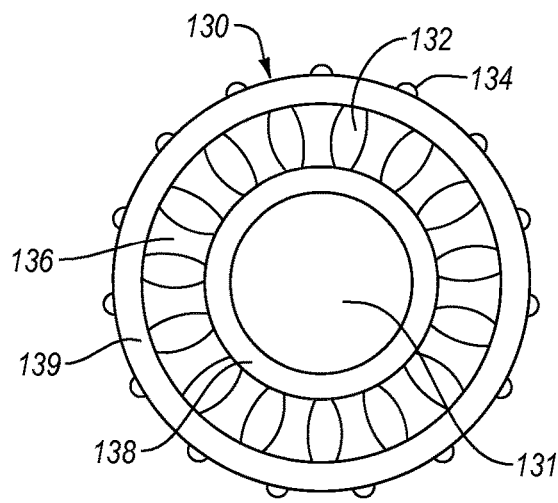
FIG. 22 is a top plan view of a cap embodiment comprising a ball type detent for use in the adjustment mechanism of FIG. 21.
Figure 23:
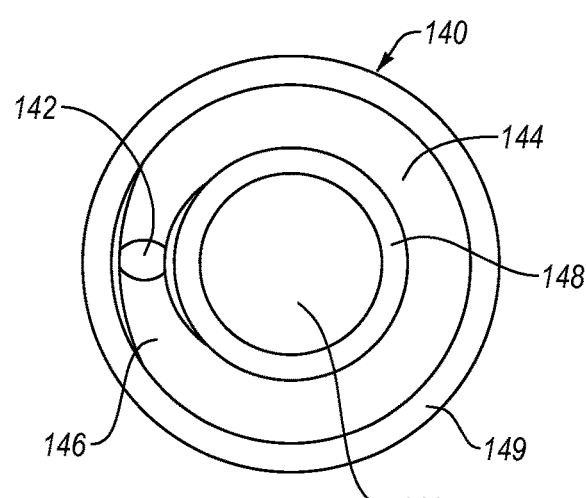
FIG. 23 is a top plan view of the inside of the cap in FIG. 22.

Referring to FIGS. 22-23, the adjustment mechanism includes a top and bottom cap 130, 140 that lock onto the dial-tensioning device via a first and second opening 131, 141, respectively. The bottom cap 140 may be circular and has a circumferential canal 144 between an inner and outer rim 148, 149 on its connecting surface. The canal 144 further includes at least one ball-shaped bump 142 on an elastic suspension 146, such as a cantilever, integrally formed. Multiple suspensions may be provided, and wherein each suspension may have a double support.

The top cap 130 is also circular and has a circumferential lip 136 on its connecting surface between an inner and outer recess 138, 139. Continuous equally spaced detent grooves 132 are circumferentially positioned on the lip 136 and are sized to engage the ball-shaped bump 142 of the bottom cap. The connecting surfaces of both the top cap 130 and the bottom cap 140 are configured to be secured to each other. In this arrangement, the lip 136 of the top cap fits within the canal 144 of the bottom cap so that when the top cap is rotated relative to the bottom cap, the ball-shaped bump 142 can releasably snap into one of the detent grooves. The inner and outer rim 148, 149 of the bottom cap are sized to fit in the inner and outer recess 138, 139 of the top cap, respectively. The top cap 130 also includes equally spaced grips 134 located circumferentially on its outer edge to make rotating easier.

The knob 125 of the dial-tensioning device can continue to rotate and reel in the torque-limiting 18 as long as the torque applied to the top cap 130 is less than a predetermined value. Once this desired torque is exceeded, the top cap 130 will freely rotate relative to the bottom cap 140, which remains secured to the knob. This unrestrained rotation prevents the knob from continuing to reel in more torque limiting.

The engagement of the ball-shaped bump 142 with the series of detent grooves 132 limits the load applied by the dial-tensioning device. A user may feel a slight ratcheting and/or slipping of the top cap 130 caused by the detent grooves 132. This transition may be audible based on the design of the ball-shaped bump and the material used. The desired torque limit can be set by increasing or decreasing the number of ball-shaped bumps 142 on the bottom cap, changing the dimensions of the ball-shaped bump and corresponding detent grooves 132, altering the shape of the ball-shaped bump and corresponding detent grooves, and/or modifying the spring force of the suspension 146.

Figure 24:
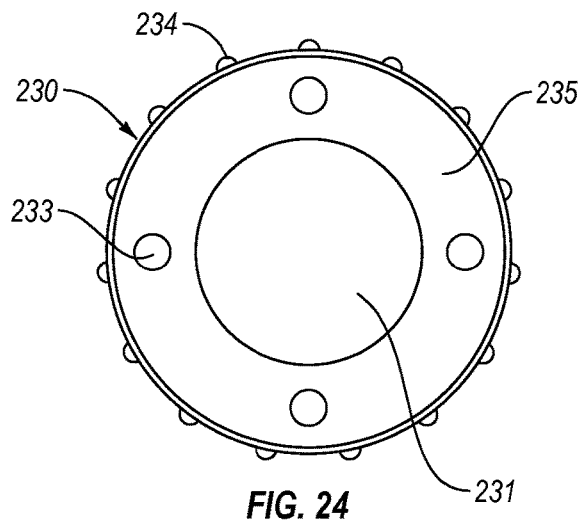
FIG. 24 is a top plan view of a cap embodiment comprising a flat band spring.
Figure 25:
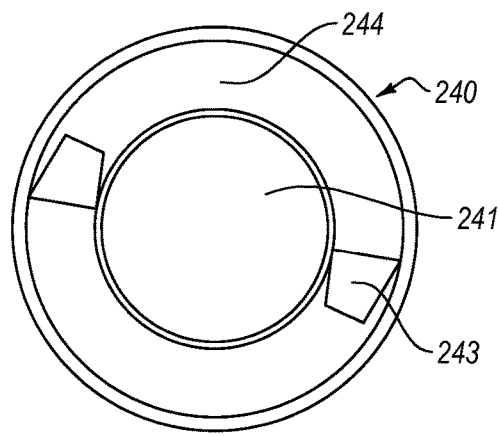
FIG. 25 is a top plan view of the inside of the cap in FIG. 24.

Turning to FIGS. 24-25, another embodiment of the adjustment mechanism is shown for controlling the torque applied to a dial-tensioning knob. A top and bottom cap 230, 240 having a first and second opening 231, 241 are provided for attachment to a dial-tensioning knob. The outer edge of the top cap 230 may further include equally spaced grips 234 located circumferentially thereon for making rotation easier for a user. The top cap includes at least one detent bump 233 on an inner recess 235 of its connecting surface. The connecting surface of the bottom cap 240 includes a guiding recess 244 having at least one angled reed 243 protruding from the surface.

Preferably, the reed 243 may be a flat spring, such as a band spring, so that in operation the detent bump 233 acts as a pressure feature to bend the spring to move past it during rotation. The required pressure exerted by the detent bump on the spring corresponds to the torque used to rotate the top and bottom caps. Exceeding the desired torque setting results in a noticeable loss of torque and a discrete audible snap after the detent bump 233 passes over and bends the flat spring 243. This sound is caused by the flat spring subsequently snapping back to its original slanted position.

By angling the spring 243, the deflection caused when the detent bump passes over it can be reduced. Preferably, the detent bump 233 should match the shape of the initial angle of the spring 243 to allow for a smooth transition. The desired torque can be set by changing the number of springs used, the dimensions of the springs, the initial spring angle, the size of the detent bump, and/or the length of the exposed spring.

Figure 26:
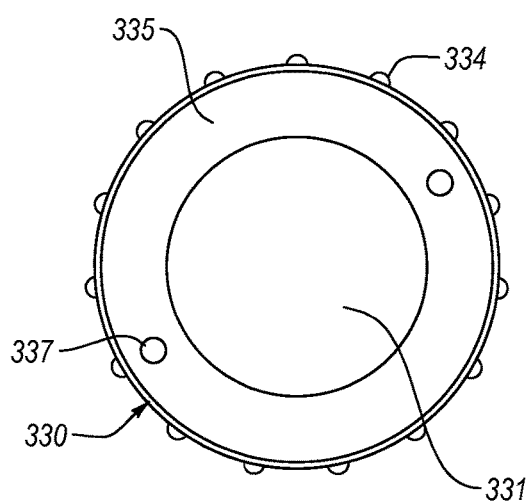
FIG. 26 is a top plan view of a cap embodiment comprising a tension coil spring.
Figure 27:
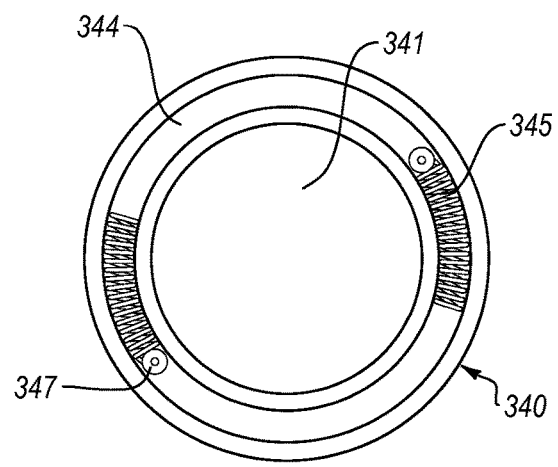
FIG. 27 is a top plan view of the inside of the cap in FIG. 26.

Yet another embodiment of the adjustment mechanism is illustrated in FIGS. 26 and 27 for controlling the torque applied to a dial-tensioning knob. A top and bottom cap 330, 340 having a first and second opening 331, 341, respectively, is provided for attachment to a dial-tensioning knob. The outer edge of the top cap 330 may include equally spaced grips 334 located circumferentially thereon for making rotation easier for a user. The top cap 330 includes at least one first anchor 337, such as a pin, on an inner recess 335 of its connecting surface.

The connecting surface of the bottom cap 340 includes a retaining recess 344 having at least one second anchor 347. The second anchor 347 may be a pin that secures one end of an elastic tension element 345, such as a tension spring. The opposite end of the tension spring secures to the at least one first anchor 337 on the top cap 330. When the torque setting exceeds the cracking force of the spring, the spring coils open up and the torque applied to the cable is limited to that allowed by the spring force. The applied torque will increase as the spring is extended during rotation of the knob. A higher spring rate will cause a greater upper limit torque setting.

Once the torque setting has been reached and the spring stretches, the top cap 330 allows the knob to be rotated up to an additional 180 degrees. The user will notice increased resistance the more the top cap is turned. Alternatively, a different spring can be used so the knob is only allowed to rotate up to an additional 90 degrees after spring engagement. When the user can no longer rotate the knob via the top cap, it has reached its full rotation allowed by the spring. The user can then let go of the top cap so the spring returns it back to its initial position. Similar to the embodiments described above, the desired torque setting can be adjusted by changing the spring wire diameter to alter its cracking force and spring rate, lengthening the spring, and/or modifying the number of springs used.

The invention claimed is:

1. A dynamic tension system for an orthopedic device having a frame and at least one hinge connected to the frame, the dynamic tension system comprising:
   a cable;
   an adjustment mechanism connected to the cable and arranged to incrementally wind or release said cable, the adjustment mechanism having front and rear sides, and the cable extending from both lateral and medial sides of the adjustment mechanism which are generally perpendicular to the front and rear sides, wherein the rear side of the adjustment mechanism is arranged to be adjacent to and face a limb upon which the orthopedic device secures;
   a tension control device connected to the front side of the adjustment mechanism and arranged to limit the adjustment mechanism from winding of the cable past a predetermined tension level;
   wherein the tension control device is a torque-limiting tool having a key part and a handle arranged to shear from the key part at a predetermined load such that upon reaching the predetermined tension level in the cable the torque-limiting tool fails by the handle shearing apart from the key part, the key part arranged to be received in and engage a keyhole defined by the adjustment mechanism for winding of the cable;
   wherein the keyhole has a matching shape corresponding to a shape of the key part;
   wherein the adjustment mechanism further includes a spool for winding the cable, the spool defining the keyhole about a face thereof along the front side of the adjustment mechanism, and defining a plurality of teeth about a periphery thereof; a base defining a cavity arranged for retaining the spool and the cavity having a profile accommodating a shape of the spool; and a pawl pivotally arranged to engage the plurality of teeth and mounted to and within the base;
   wherein the base defines an opening extending through the base from a rear side of the base to a front side of the base, which the rear side of the base is arranged to be adjacent to and face a limb upon which the orthopedic device secures such that access to the pawl through the opening of the base for disengaging the pawl from the spool is prevented.

2. The dynamic tension system of claim 1, wherein the adjustment mechanism further comprises:
   a spring engaging the pawl and biasing the pawl toward the plurality of teeth, a first end of the spring biasing against the base and an opposed second end of the spring biasing against the pawl.

3. The dynamic tension system of claim 2, wherein the base defines an enclosure arranged to receive and retain the first end of the spring.

4. The dynamic tension system of claim 1, wherein the base defining a boss about which the spool rotates.

5. The dynamic tension system of claim 1, wherein the base defines a pin at which a first end of the pawl pivots so an opposed second end of the pawl can engage or disengage from the plurality of teeth.

6. The dynamic tension system of claim 1, wherein the base defines at least one channel arranged to direct movement of the cable relative to the base and from the spool.

7. The dynamic tension system of claim 1, further comprising a shroud arranged to cover the adjustment mechanism, on the front side of the adjustment mechanism and having an opening arranged for providing access to the adjustment mechanism.

8. The dynamic tension system of claim 7, wherein the tension control device is adapted to extend through the opening of the shroud to engage the adjustment mechanism and selectively rotate the spool.

9. The dynamic tension system of claim 7, further comprising a plate arranged to selectively secure over the opening of the shroud to prevent access to the adjustment mechanism.

10. The dynamic tension system of claim 1, further comprising a sheathing arranged over at least one segment of the cable outside the adjustment mechanism.

11. The dynamic tension system of claim 1, wherein a first end of the cable secures to a first hinge of the at least one hinge of the orthopedic device and a second end of the cable secures to a second hinge of the at least one hinge of the orthopedic device and the cable passes through the adjustment mechanism, the adjustment mechanism connected to the frame and movable relative thereto on the basis of winding the cable and/or movement of the at least one hinge.

12. The dynamic tension system of claim 11, further comprising at least one guide secured to the frame and orienting the cable relative to the frame, the at least one hinge and the adjustment mechanism, the cable extending generally perpendicular to the frame between the adjustment mechanism and the at least one guide.

* * * * *